(12) United States Patent  (10) Patent No.: US 8,618,281 B2
Lindsey et al.  (45) Date of Patent: Dec. 31, 2013

(54) GEOMETRIC SYNTHESIS OF PORPHYRIN RODS

(75) Inventors: Jonathan S. Lindsey, Raleigh, NC (US); Lianhe Yu, Highpoint, NC (US); Patchanita Thamyongkit, Bangkok (TH); Anil D. Bhise, Pune (IN)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 13/600,808

(22) Filed: Aug. 31, 2012

(65) Prior Publication Data

US 2013/0079528 A1  Mar. 28, 2013

Related U.S. Application Data

(62) Division of application No. 13/074,483, filed on Mar. 29, 2011, now Pat. No. 8,288,529, which is a division of application No. 12/856,020, filed on Aug. 13, 2010, now Pat. No. 7,939,656, which is a division of application No. 11/324,719, filed on Jan. 3, 2006, now Pat. No. 7,799,910.

(51) Int. Cl.
C07D 487/22 (2006.01)
C07B 47/00 (2006.01)

(52) U.S. Cl.
USPC ......................................................... 540/145

(58) Field of Classification Search
USPC ......................................................... 540/145
See application file for complete search history.

(56) References Cited

U.S. PATENT DOCUMENTS

| | | |
|---|---|---|
| 6,420,648 B1 | 7/2002 | Lindsey |
| 6,603,070 B2 | 8/2003 | Lindsey et al. |
| 6,849,730 B2 | 2/2005 | Lindsey et al. |
| 7,022,862 B2 | 4/2006 | Lindsey et al. |

OTHER PUBLICATIONS

Thamyongkit, P, et al., Alkylthio unit as an α-pyrrole protecting group for use in dipyrromethane synthesis, J. Org. Chem. (2006) 903-910, 71.

Setsune, J and Hashimoto, M, Synthesis and separation of meso-tetraarylporphyrins with $C_1$ symmetry, J. Chem. Soc., Chem. Commun. (1994) 657-658.
Setsune, J, et al., Synthesis and atropisomerism of meso-tetraarylporphyrins with mixed meso-aryl grops having ortho-substituents, Tetrahedron (1998) 1407-1424, 54.
International Search Report and Written Opinion for corresponding International Application PCT/US/06/46024 (Mar. 12, 2007).

Primary Examiner — Paul V. Ward
(74) Attorney, Agent, or Firm — Myers Bigel Sibley & Sajovec, P.A.

(57) ABSTRACT

A method of making a compound of Formula I'

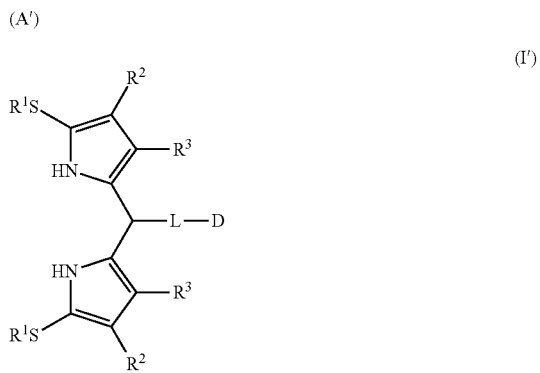

comprises reacting a compound of the formula DLCHO, with a compound of the formula

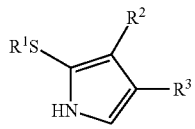

to produce the compound of Formula I'. Methods of using the compounds are also described, particularly as intermediates for the synthesis of porphyrin rods, which porphyrin rods are in turn useful for (among other things) the production of molecular memory devices.

7 Claims, No Drawings

GEOMETRIC SYNTHESIS OF PORPHYRIN RODS

RELATED APPLICATIONS

This application is a divisional of and claims priority to U.S. patent application Ser. No. 13/074,483, filed Mar. 29, 2011, now U.S. Pat. No. 8,288,529, which is a divisional of U.S. patent application Ser. No. 12/856,020, filed Aug. 13, 2010, now U.S. Pat. No. 7,939,656, which is a divisional of U.S. patent application Ser. No. 11/324,719, filed Jan. 3, 2006, now U.S. Pat. No. 7,799,910, the disclosure of each of which is incorporated by reference herein in its entirety.

GOVERNMENT FUNDING

This invention was made with government support under grant number GM-36238 from the National Institutes of Health. The US Government has certain rights to this invention.

FIELD OF THE INVENTION

This invention concerns-1,9-bis(thio)dipyrromethanes, methods of making the same, and methods of using the same in the geometric synthesis of porphyrin rods.

BACKGROUND OF THE INVENTION

The synthesis of porphyrinic macrocycles and related compounds requires the ability to carry out reactions at the pyrrolic α- and α'-positions (2- and 5-positions, respectively). The controlled introduction of a single substituent via electrophilic substitution can necessitate the use of a blocking group, particularly when the newly introduced substituent activates the pyrrole to further substitution. In the synthesis of naturally occurring porphyrins, which typically entails the use of 3,4-disubstituted pyrroles (e.g., A), an ester (or carboxylic acid) suffices to block the 2-position: substitution occurs at the 5-position, which contains the only open carbon in the pyrrolic nucleus (eq 1). Removal of the blocking carboxy moiety typically requires treatment at high temperature with a strong base, a strong acid, and/or a halogen reagent. Use of the halogen reagent affords the 2-halopyrrolic species, which is converted to the pyrrole with the open 2-position by catalytic hydrogenation (Paine, J. B., III. In *The Porphyrins*; Dolphin, D. Ed.; Academic Press: New York, 1978; Vol. I, pp 101-234). In general, the use of a carboxylate (or other electron-withdrawing group) to block the 2-position in a pyrrole lacking substituents at the 3- and 4-positions (e.g., B, eq 2) is expected to present three problems: (1) sluggish reaction, (2) diminished selectivity for the direction of the incoming group to the 5-position vs the 4-position, and (3) harsh conditions for removal of the carboxylate group.

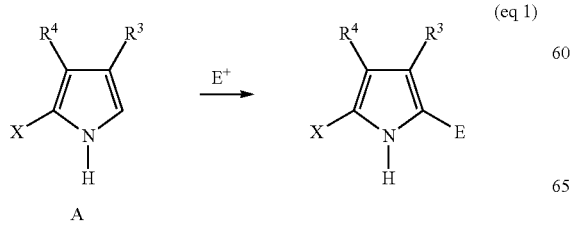

(eq 1)

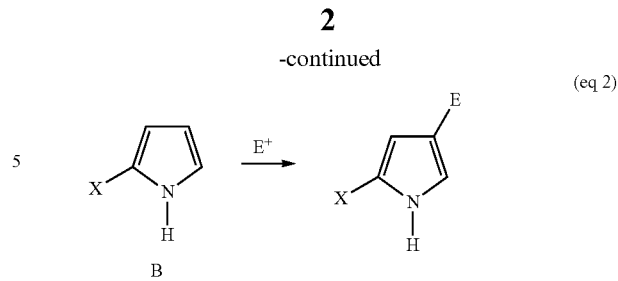

(eq 2)

To our knowledge, only one β-unsubstituted dipyrromethane has been prepared via this approach (Setsune, J.-i. et al., *J. Chem. Soc., Chem. Commun.* 1994, 657-658; Setsune, J.-i. et al., *Tetrahedron* 1998, 54, 1407-1424). On the other hand, the incoming group could be directed rapidly to the 5-position with an α-blocking group that is not deactivating, but such a simple protective group for pyrroles has heretofore not been developed.

The absence of a suitable α-blocking group for unsubstituted pyrroles has substantially affected a number of synthetic transformations. For example, the synthesis of β-unsubstituted dipyrromethanes is typically carried out by reaction of an aldehyde with excess pyrrole (up to 100 mol equiv), resulting in 1, N-confused dipyrromethane 2, tripyrrane 3, and oligomeric byproducts (Scheme i).

Scheme i

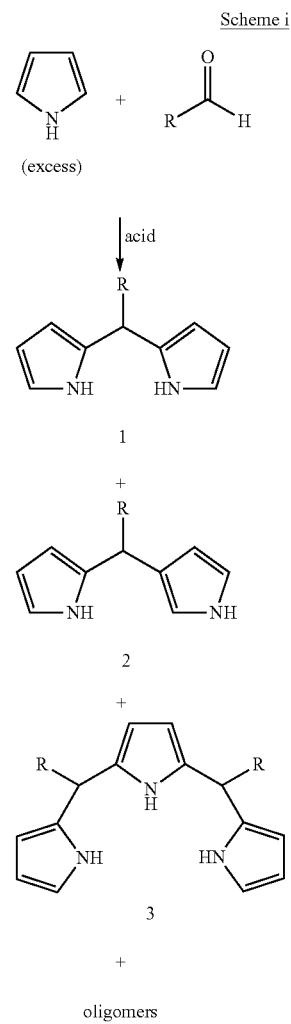

The presence of excess pyrrole is required to trap the initially formed pyrrole-carbinol and thereby suppress the competitive self-oligomerization of the pyrrole-carbinol. Although considerable refinement has gone into streamlining the conditions for carrying out this reaction and purifying the product (Lee, C. H.; Lindsey, J. S. *Tetrahedron* 1994, 50, 11427-11440; Littler, B. J. et al., *J. Org. Chem.* 1999, 64, 1391-1396; Laha, J. K. et al., *Org. Process Res. Dev.* 2003, 7, 799-812), the use of such a large excess of pyrrole remains an inherent disadvantage. The availability of a blocking group that is not deactivating would enable the use of a stoichiometric amount of the protected pyrrole (2 mol equiv) and the aldehyde. Thompson and co-workers have recently reported a sulfonyl or 2,4-dinitrophenylsulfinyl group for protecting the α-pyrrole position, but again, both groups are deactivating (Thompson, A. et al., *J. Org. Chem.* 2005, 70, 3753-3756).

SUMMARY OF THE INVENTION

A first aspect of the present invention is a method of making a compound of Formula I':

(A')

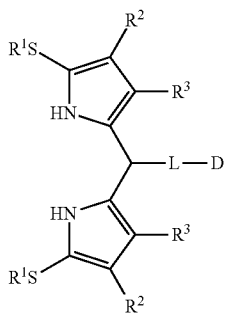

(I')

wherein:

D, $R^1$, $R^2$, and $R^3$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, acyloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups (with linking groups, surface attachment groups, bioconjugatable groups, targeting groups and water soluble groups less preferred for $R^1$);

or D is a group of the formula:

(D)

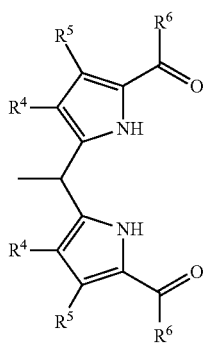

wherein $R^4$, $R^5$, and $R^6$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups; and L is a linker or covalent bond;

the method comprising:

reacting a compound of the formula DLCHO, wherein D and L are as given above, with a compound of the formula:

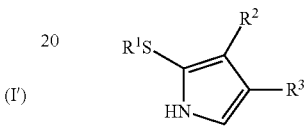

wherein $R^1$, $R^2$ and $R^3$ are as given above, to produce said compound of Formula I'.

A second aspect of the invention is a method of making a compound of Formula I:

(A)

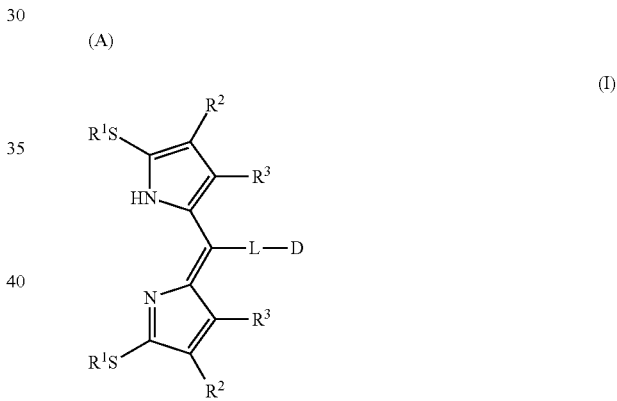

(I)

wherein D, $R^1$, $R^2$, $R^3$ and L are as given above, said method comprising oxidizing a compound of Formula I' as given above to produce the compound of Formula I.

Further aspects of the invention is a method of making a compound of Formula II:

(C)

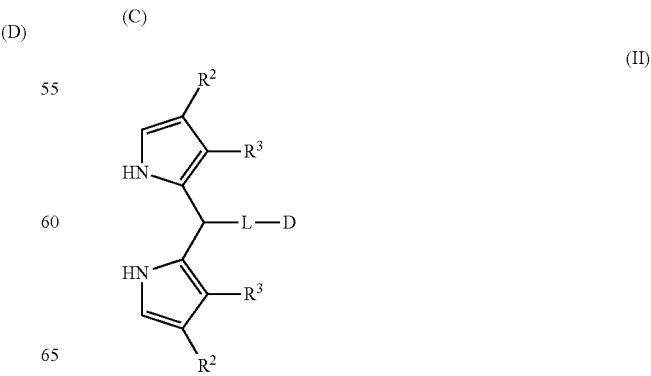

(II)

wherein D, $R^2$, $R^3$, and L are as given above, the method comprising desulfurizing and reducing (in any order) a compound of Formula I as given above, or desulfurizing a compound of Formula I' as given above to produce said compound of Formula II.

The compounds are useful, among other things, as intermediates in the synthesis of porphyrin rods, which are in turn useful for the preparation of molecular memory devices.

The present invention is explained in greater detail below.

DETAILED DESCRIPTION OF THE PREFERRED EMBODIMENTS

The disclosures of all United States Patent references cited herein are to be incorporated by reference herein as if fully set forth.

"Acyl" is intended to mean a —C(O)—R group, where R is a suitable substituent such as H, alkyl or aryl, which may in turn be substituted or unsubstituted.

"Dipyrromethane" as used herein includes an unsubstituted or substituted dipyrromethane, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc.

"Dipyrrin" as used herein includes an unsubstituted or substituted dipyrrin, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 1 or 2 to 10, 20 or 50 carbon atoms (e.g., C1 to C4 alkenyl; C4 to C10 alkenyl; C11 to C50 alkenyl) (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone or as part of another group, refers to a straight or branched chain hydrocarbon containing from 1 or 20 to 10, 20 or 50 carbon atoms (e.g., C1 to C4 alkynyl; C4 to C10 alkynyl; C11 to C50 alkynyl) (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)$NR_aR_b$ radical, where $R_a$ and $R_b$ are any suitable substituent such as H, alkyl, cycloalkyl, alkenyl, alkynyl or aryl.

"Sulfonamide" as used herein alone or as part of another group refers to a —S(O)$_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —N($R_c$)C(O)$NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —N($R_a$)C(O)$OR_b$ radical, where $R_a$ and $R_b$ are any suitable substituent such as H, alkyl, cycloalkyl, alkenyl, alkynyl or aryl.

"Aminoacyloxy" as used herein alone or as part of another group refers to an —OC(O)$NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl)monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

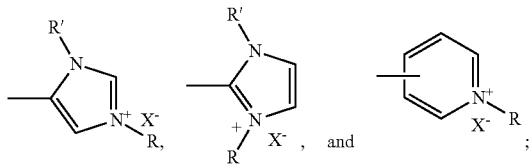

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—$PO_3H_2$) or sulfonic acid (—$SO_3H$), and $X^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —$CH_2CH_2CH_2$—, —$CH_2CH_2CH_2CH_2$—, —$CH_2CH_2CH_2CH_2CH_2$—, —$CH_2CH_2CHCHCH_2$—, —$CH_2CH_2CH_2CH_2CH_2CH_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1 or 2.

"Aldehyde" as used herein refers to a group of the formula:

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and $NH_4Cl$.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula $LnX_3$ where Ln is a lanthanide and X is halo such as Cl, Br, I, etc., triflate or OTf, etc., and with examples specific examples including but not limited to: Yb(OTf)$_3$, InCl$_3$, Sc(OTf)$_3$, MgBr$_2$ and CeCl$_3$.

"Porphyrinic macrocycle" refers to a porphyrin or porphyrin derivative, and are discussed in greater detail below.

"Macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings). The macrocyclic ligand may be in the form of a substituent. See, e.g., U.S. Pat. No. 6,411,164 to Sibert.

"Crown ether" as used herein means a macrocyclic polyether whose structure exhibits a conformation with a so-called hole capable of trapping cations by coordination with a lone pair of electrons on the oxygen atoms (see generally McGraw-Hill Dictionary of Scientific and Technical Terms (3d ed. 1984)). Crown ethers are a species of macrocyclic ligand. The crown ether may be in the form of a substituent. See, e.g., U.S. Pat. No. 6,411,164 to Sibert.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates)

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis*, 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, acetyl (Ac or —C(O)CH$_3$), benzoyl (Bn or —C(O)C$_6$H$_5$), and trimethylsilyl (TMS or —Si(CH$_3$)$_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724.

"Coupling agent" as used herein, refers to a reagent capable of coupling a photosensitizes to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers", or "linker groups" (e.g., L above) are aromatic or aliphatic groups (including both saturated and unsaturated aliphatic groups) (which may be substituted or unsubstituted and may optionally contain heteroatoms such as N, O, or S) that are utilized to couple a bioconjugatable group, crosscoupling group, surface attachment group, hydrophilic group or the like to the parent molecule. Examples include but are not limited to aryl (such as p-phenylene), alkyl, heteroaryl, heteroalkyl (e.g., oligoethylene glycol), peptide, and polysaccharide linkers, etc. A "linker" may contain one or more porphyrinic groups as discussed further below.

"Water soluble group" as used herein generally includes substituents containing at least one ionic or polar group, coupled to the parent molecule directly or by means of an intervening linker. Examples include but are not limited to groups of the formula:

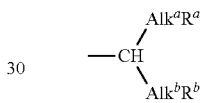

wherein $R^a$ and $R^b$ are each independently an ionic group or polar group, and $Alk^a$ and $Alk^b$ are each independently a C1-050 alkylidene chain.

1. Scheme 1 Reactions.

The present invention provides a set of reactions summarized in Scheme 1 each of which is discussed in further detail below.

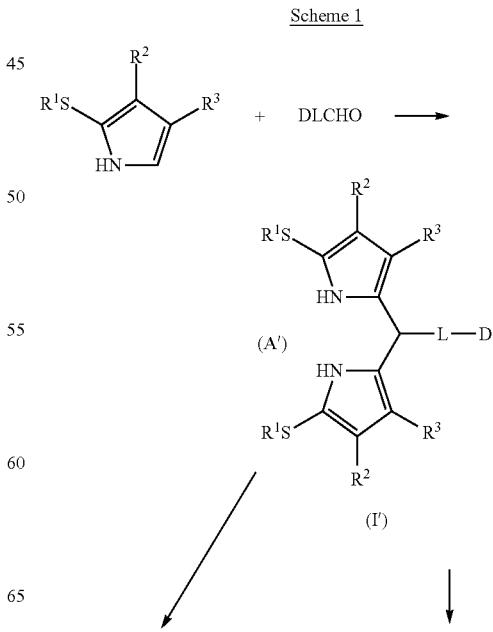

Scheme 1

-continued

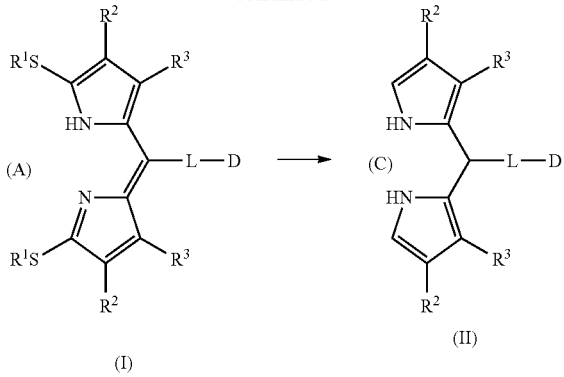

As will be seen from the top portion of Scheme I, a first aspect of the present invention is a method of making a compound of Formula I':

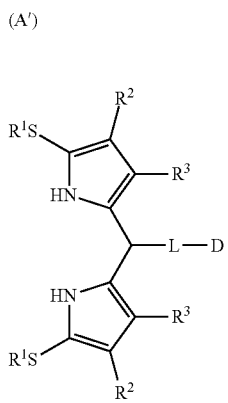

wherein:

D, $R^1$, $R^2$, and $R^3$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups (with linking groups, surface attachment groups, bioconjugatable groups, targeting groups and water soluble groups less preferred for $R^1$);

or D is a group of the formula:

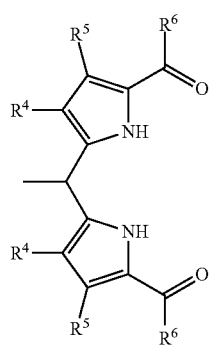

wherein $R^4$, $R^5$, and $R^6$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups; and L is a linker or covalent bond;

the method comprising:

reacting a compound of the formula DLCHO, wherein D and L are as given above, with a compound of the formula:

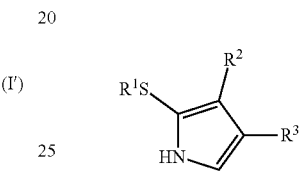

wherein $R^1$, $R^2$ and $R^3$ are as given above, to produce said compound of Formula I'. The reacting step may be carried out with or without a solvent (including any suitable organic solvent) in the presence of an acid, typically a mild Lewis or Bronsted acid, at any suitable temperature (e.g., room temperature).

As will be seen from the reaction indicated by the diagonal arrow in Scheme I, a second aspect of the invention is a method of making a compound of Formula I:

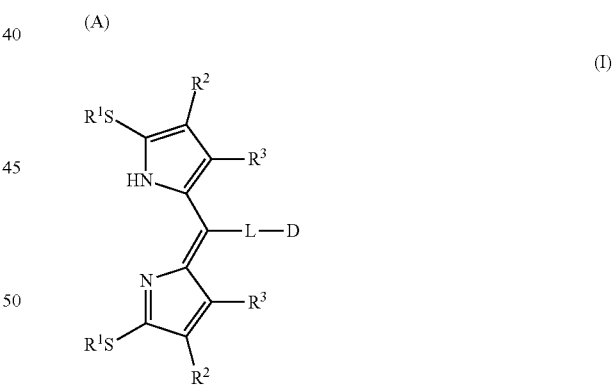

wherein D, $R^1$ $R^2$, $R^3$ and L are as given above, said method comprising oxidizing a compound of Formula I' as given above to produce the compound of Formula I. The oxidizing step can be carried out by any suitable means, such as with 2,3-dichloro-5,6-dicyano-1,4-benzoquinone (DDQ) or chloranil (o- or p-chloranil) as an oxidizing agent, typically in an organic solvent (e.g., THF, toluene, methylene chloride, mixtures thereof).

Further, and as is exemplified by the two arrows pointing to the compound in the bottom right corner if Scheme I, a further aspect of the invention is a method of making a compound of Formula II:

(C)

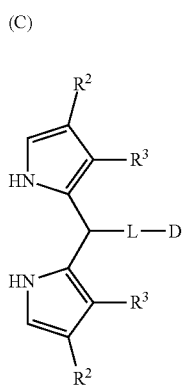

(II)

wherein D, $R^2$, $R^3$, and L are as given above. In one embodiment the method comprises desulfurizing and reducing (in any order) a compound of Formula I as given above to produce the compound of Formula II. In another embodiment, the method comprises desulfurizing a compound of Formula I' as given above to produce said compound of Formula II. The reducing step may be carried out with any suitable reducing agent, such as sodium borohydride (titrated to protect the keto groups). A preferred reducing agent is sodium dithionite ($Na_2S_2O_4$).

The desulfurizing step is (or removal of the thio groups $R^1S-$) can be carried out by any suitable means, such as with a metallic or organometallic desulfurizing reagent in any suitable solvent (e.g., THF), such as described by Sucholeiki, I. *Tetrahedron Lett.* 1994, 40, 7307-7310. The thio group can be cleaved from the parent molecule, or the parent molecule desulfurized, by any suitable technique, such as with a metallic or organometallic reagent, including but not limited to such as nickel, lithium, potassium, iron, cobalt, molybdenum, rhodium, titanium, manganese and osmium compounds. Among these reagents, nickel are preferred, with Raney nickel particularly preferred. Other approaches to desulfurization include but are not limited to conversion of the thio group to the corresponding sulfone, which is also readily cleaved by metallic or organometallic reagents. See generally Bougault, J. et al., *Bull. Soc. Chim. Fr.* 1939, 6, 34; Pettit, G. R.; van Tamelen, E. E. *Org. React.,* 1962, 12, 356-529; Hauptmann, H.; Walter, W. F. *Chem. Rev.* 1962, 63, 347-404; Wenkert, E.; Ferreira, T. W. *J. Chem. Soc., Chem. Commun.* 1982, 840-841; Truce, W. E.; Roberts, F. E. *J. Org. Chem.* 1963, 28, 961-964; Eisch, J. J.; Im, K. R. *J. Organomet. Chem.* 1977, 139, C51-C55; Chan, M.-C. et al., *J. Org. Chem.* 1988, 53, 4466-4471; Becker, S. et al., *Tetrahedron. Lett.* 1988, 29, 2963-2966; Ho, K. M. et al., *J. Org. Chem.* 1989, 54, 4474-4476; Gilman, H.; Esmay, D. L. *J. Am. Chem. Soc.* 1953, 75, 2947-2949; Eisch, J. J. *J. Org. Chem.* 1963, 28, 707-710; Ignasiak, T. et al., *J. Org. Chem.* 1977, 42, 312-320; Alper, H. *J. Org. Chem.* 1975, 40, 2694; Alper, H.; Paik, H.-N. *J. Org. Chem.* 1977, 42, 3522-3524; Alper, H. et al., *Tetrahedron Lett.* 1983, 24, 5329-5332; Shim, S. C.; Antebi, S.; Alper, H. *J. Org. Chem.* 1985, 50, 147-149; Shim, S. C. et al., *Tetrahedron Lett.* 1985, 26, 1935-1938; Yeung, L. L. et al., *J. Chem. Soc., Chem. Commun.* 1987, 981-983; Luh, T.-Y.; Wong, C. S. *J. Org. Chem.* 1985, 50, 5413-5415; Osakada, K. et al., *Organometallics* 1985, 4, 857-862; Kilanowski, D. et al., *J. Catal.* 1978, 55, 129-137; Mukaiyama, T. et al., *Chem. Lett.* 1973, 291-294; Alper, H. *J. Organomet. Chem.* 1974, 73, 359-364; Adams, R. D. et al., *Organometallics* 1982, 1, 235-239.

In some preferred embodiments of the foregoing, $R^1$ is alkyl, cycloalkyl, or cyano.

In some preferred embodiments of the foregoing, D is a surface attachment group.

In some preferred embodiments of the foregoing, $R^6$ is H, alkyl, or aryl.

2. Additional Reactions.

A 1,9-diacyldipyrromethane is reduced to produce a dipyrromethane-1,9-dicarbinol, as shown in Scheme 2, in accordance with known techniques. In general the reducing step is carried out by treating the 1,9-diacyldipyrromethane with any suitable reductant (such as $NaBH_4$) to form the dipyrromethane-1,9-dicarbinol.

Scheme 2

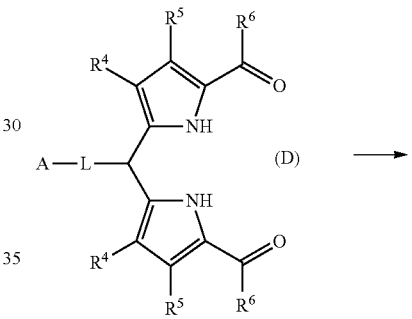

(D)

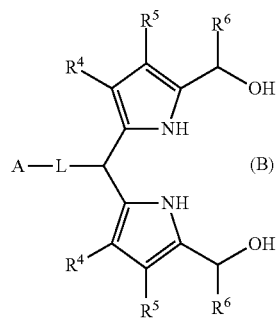

(B)

Substituents in Scheme 2 are the same as given in section 1 above.

A dipyrromethane can be condensed with a dipyrromethane-1,9-dicarbinol to produce a porphyrin, as shown in Scheme 3, in accordance with known techniques, including but not limited to those described in U.S. Pat. No. 6,849,730 to Lindsey et al.

Scheme 3

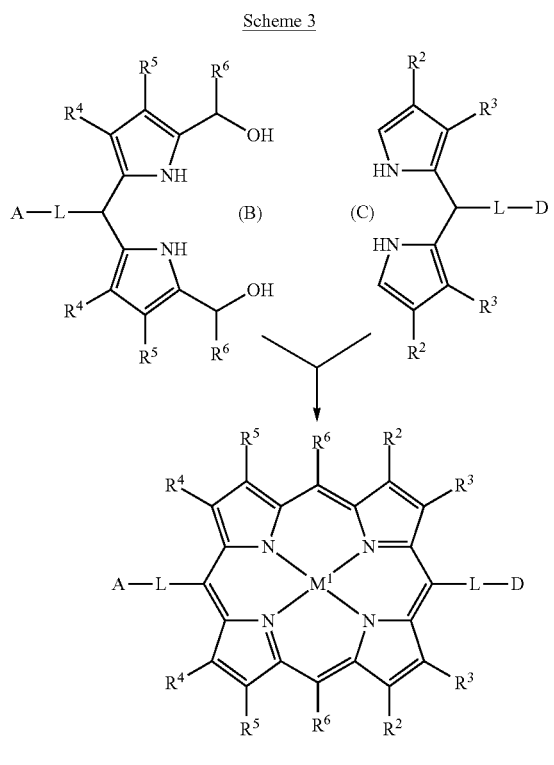

Substituents in Scheme 3 are the same as given in section 1 above.

3. Synthesis of Porphyrin Rods.

As noted in this section, the reactions set forth in section 1 above can be used in combination with the reactions set forth in section 2 above to provide methods for the synthesis of porphyrin rods. One embodiment of such a set of reactions is set forth in Scheme 4:

Scheme 4

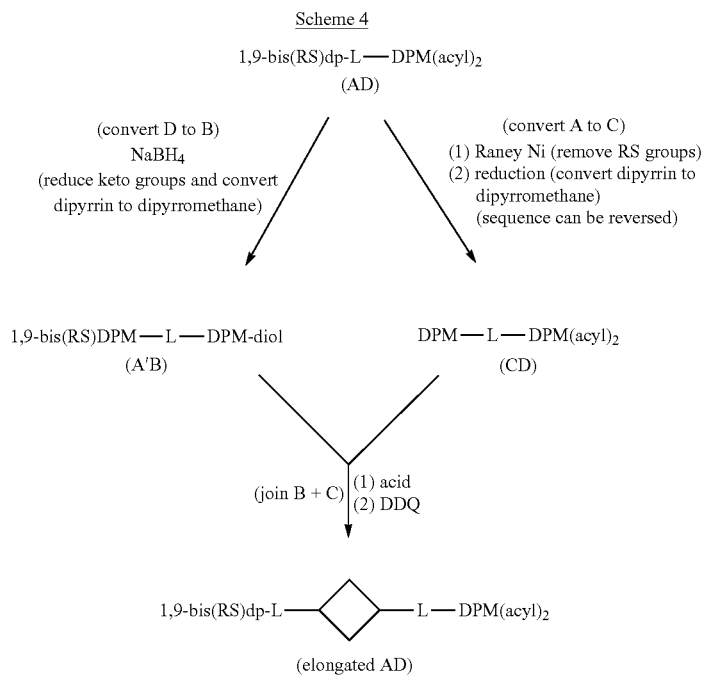

As shown schematically in Scheme 5, the series of reactions summarized in Scheme 4 can be repeated in a geometric synthesis to build up a series of oligomers. The number of porphyrins ($S_n$) in the resulting series of oligomers is 1, 3, 7, 15, 31, 63 ... and is given in general by equation 1, $$S_n = 2^n - 1 \tag{1}$$

where n=the number of cycles.

Scheme 5

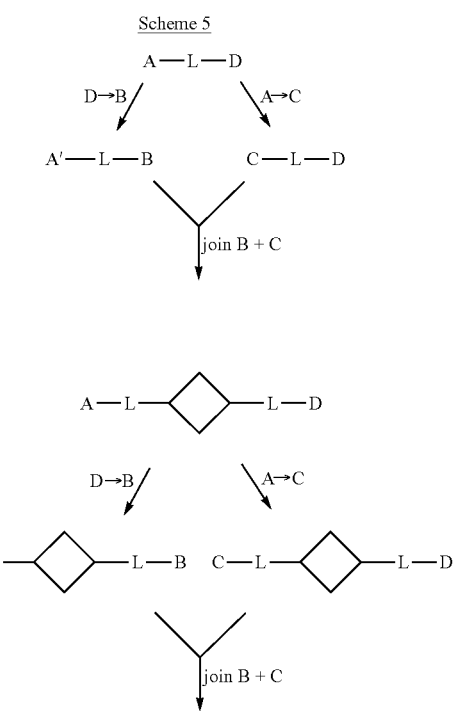

19
-continued
20
-continued
5 (symbolizes a porphyrin)
One specific embodiment of the reactions given in Scheme 5 is set forth in Scheme 6 below, where A, B, C, D, L, $R^1$, $R^2$, $R^3$, $R^4$, $R^5$, and $R^6$ are as given above.
Scheme 6
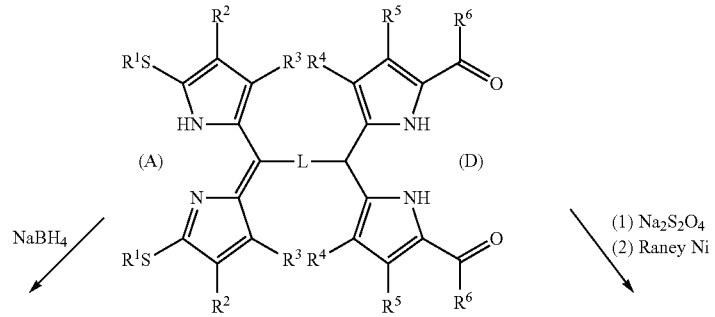
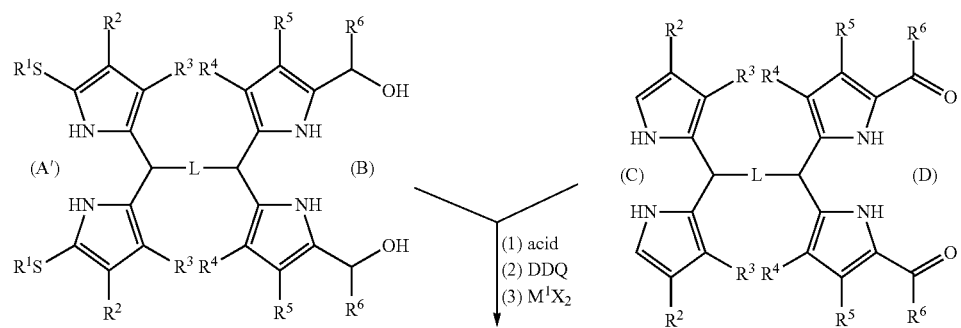
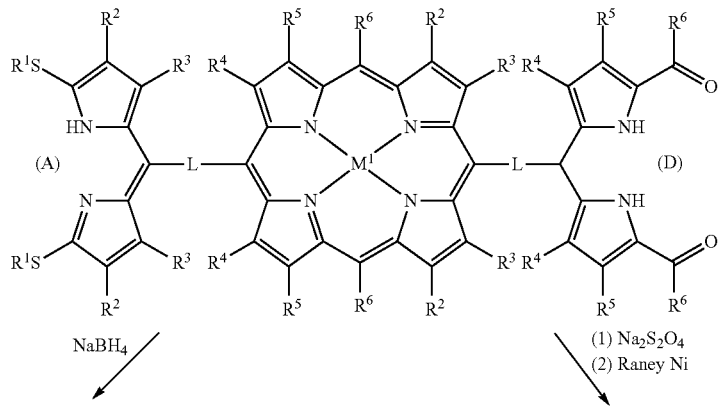

-continued

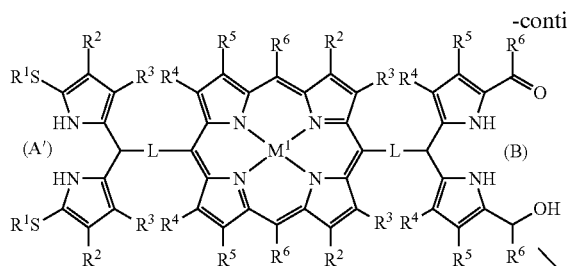

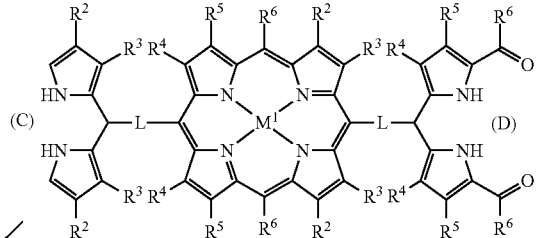

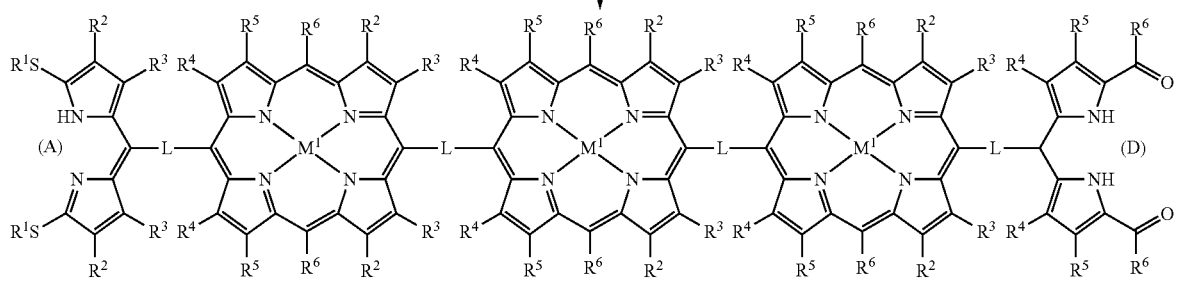

wherein L is a linking group or covalent bond; $M^1$ is a metal or is absent; and $R^1$, $R^2$, $R^3$, $R^4$, $R^5$ and $R^6$ are as given above. In some embodiments, $R^1$ is alkyl, cycloalkyl, or cyano. In some embodiments, $R^6$ is H, alkyl, or aryl. In some embodiments, L is a covalent bond.

As summarized in Schemes 4-6, and utilizing the methods described above, a method for the synthesis of a porphyrin rod comprises the steps of:
  (a) providing a compound of the formula A-L-D, wherein A is a 1,9-bis(thio)dipyrrin, L is a linker group or covalent bond, and D is a 1,9-diacyldipyrromethane;
  (b) reducing the compound of formula A-L-D to produce a compound of the formula A'-L-B, wherein A is a 1,9-bis(thio)dipyrromethane, L is the linker group or covalent bond, and B is a dipyrromethane-1,9-dicarbinol;
  (c) desulfurizing and reducing (in any order) the compound of formula A-L-D to produce a compound of the formula C-L-D; wherein C is a dipyrromethane, L is the linker group or covalent bond, and D is a 1,9-diacyldipyrromethane;
  (d) condensing the compound of formula A'-L-B with the compound of formula C-L-D to produce an elongated compound of formula A-L-D, wherein A is a 1,9-bis(thio)dipyrrin, L is a linker group, and D is a 1,9-diacyldipyrromethane, with the linker group comprising $2^n-1$ porphyrinic macrocycles, wherein n is from 1 to 4, 5, 10 or 20 or more; and then
  (e) optionally repeating steps (b) through (d) for 2 to 10 additional cycles to produce a further elongated compound of formula A-L-D.

In some embodiments, the method further comprises the steps of:
  (f) reducing the elongated compound of formula A-L-D to produce an elongated compound of the formula A'-L-B, wherein A is a 1,9-bis(thio)dipyrromethane, L is the linker group or covalent bond, and B is a dipyrromethane-1,9-dicarbinol;
  (g) reacting the elongated compound of formula A'-L-B with a dipyrromethane (substituted or unsubstituted such as with a surface attachment group) to produce a compound of the formula A-L-E, wherein E is a porphyrinic macrocycle;
  (h) desulfurizing and reducing the compound of formula A-L-E to produce a compound of formula C-L-E, wherein C is a dipyrromethane; then
  (i) reacting the compound of formula C-L-E with a dipyrromethane-1,9-dicarbinol (substituted or unsubstituted such as with a surface attachment group) to produce a compound of the formula F-L-E, wherein F is a porphyrinic macrocycle; and optionally, where the compound of formula F-L-E contains at least one surface attachment group (that is, at least one substitutent is a covalently coupled surface attachment group),
  (j) coupling the compound of formula F-L-E to a substrate (such as a metallic, conductive, or semiconductor substrate) to produce a molecular memory device.

In other embodiments of the method described above, the method may further comprise the steps of:
  (f) desulfurizing (e.g., with a metallic or organometallic reagent as described above) and reducing (in any order) the elongated compound of formula A-L-D to produce an elongated compound of formula C-L-D; wherein C is a dipyrromethane, L is the linker group or covalent bond, and D is a 1,9-diacyldipyrromethane;
  (g) reacting the compound of formula C-L-D with a dipyrromethane-1,9-dicarbinol (substituted or unsubstituted such as with a surface attachment group) to produce a compound of the formula F-L-D, wherein F is a porphyrinic macrocycle;
  (h) reducing the compound of formula F-L-D to produce a compound of formula F-L-B, wherein B is a dipyrromethane-1,9-dicarbinol;
  (i) reacting the compound of formula F-L-B with a dipyrromethane (substituted or unsubstituted such as with a surface attachment group) to produce a compound of the formula F-L-E, wherein E is a porphyrinic macrocycle, and optionally, where the compound of formula F-L-E contains at least one surface attachment group, (j) coupling the compound of formula F-L-E to a substrate (such as a metallic, conductive, or semiconductor substrate) to produce a molecular memory device.

As will also be seen from Schemes 3-6 above, the present invention also provides a method for the synthesis of a porphyrin rod, comprising the steps of:

(a) providing a compound of the formula A'-L-B, wherein A is a 1,9-bis(thio)dipyrromethane, L is a linker group or covalent bond, and B is a dipyrromethane-1,9-dicarbinol;

(b) providing a compound of the formula C-L-D; wherein C is a dipyrromethane, L is a linker group or covalent bond, and D is a 1,9-diacyldipyrromethane or surface attachment group;

(c) condensing the compound of formula A'-L-B with the compound of formula C-L-D to produce an elongated compound of formula A-L-D, wherein A is a 1,9-bis(thio)dipyrrin, L is a linker group, and D the a 1,9-diacyldipyrromethane or surface attachment group, with the linker group comprising at least one porphyrinic macrocycle. Various groups may be substituted or unsubstituted as described above.

In some embodiments the method further comprises the steps of:

(d) reducing the elongated compound of formula A-L-D to produce an elongated compound of the formula A'-L-B, wherein A is a 1,9-bis(thio)dipyrromethane, L is the linker group or covalent bond, and B is a dipyrromethane-1,9-dicarbinol;

(e) reacting the elongated compound of formula A'-L-B with a dipyrromethane to produce a compound of the formula A-L-E, wherein E is a porphyrinic macrocycle;

(f) desulfurizing and reducing the compound of formula A-L-E to produce a compound of formula C-L-E, wherein C is a dipyrromethane;

(g) reacting the compound of formula C-L-E with a dipyrromethane-1,9-dicarbinol to produce a compound of the formula F-L-E, wherein F is a porphyrinic macrocycle; and optionally, when the compound of formula F-L-E contains at least one surface attachment group;

(h) coupling the compound of formula F-L-E to a substrate (such as a metallic, conductive, or semiconductor substrate) to produce a molecular memory device.

In other embodiments the method further comprising the steps of:

(d) desulfurizing and reducing the elongated compound of formula A-L-D to produce an elongated compound of the formula C-L-D; wherein C is a dipyrromethane, L is the linker group or covalent bond, and D is a 1,9-diacyldipyrromethane;

(e) reacting the compound of formula C-L-D with a dipyrromethane-1,9-dicarbinol to produce a compound of the formula F-L-D, wherein F is a porphyrinic macrocycle; and then (f) reducing the compound of formula F-L-D to produce a compound of formula F-L-B, wherein B is a dipyrromethane-1,9-dicarbinol;

(g) reacting the compound of formula F-L-B with a dipyrromethane to produce a compound of the formula F-L-E, wherein E is a porphyrinic macrocycle; and optionally, when the compound of formula F-L-E contains at least one surface attachment group, (h) coupling the compound of formula F-L-E to a substrate (such as a metallic, conductive, or semiconductor substrate) to produce a molecular memory device.

In some embodiments of the foregoing, for the compound of the formula A-L-D:

A is a group of the formula:

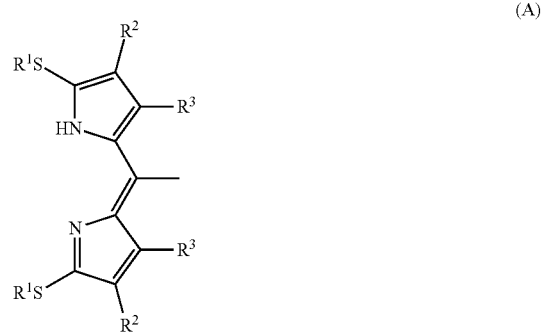

wherein $R^1$, $R^2$, and $R^3$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

L is a linker group or covalent bond; and

D is a group of the formula:

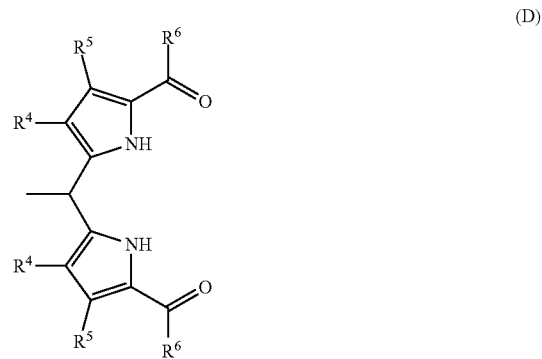

wherein $R^4$, $R^5$, and $R^6$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups.

In some embodiments of the foregoing, for the compound of the formula A'-L-B:

A' is a group of the formula:

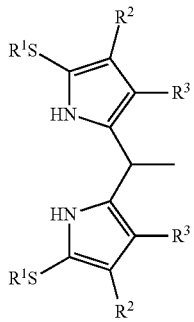

(A')

wherein $R^1$, $R^2$, and $R^3$ are as given above;

L is a linker group or covalent bond; and

B is a group of the formula:

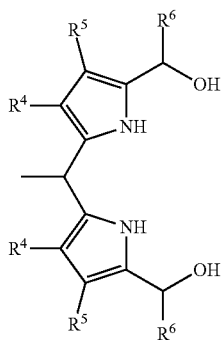

(B)

wherein $R^4$, $R^5$, and $R^6$ are as given above.

In some embodiments of the foregoing, for the compound of the formula C-L-D:

C is a group of the formula:

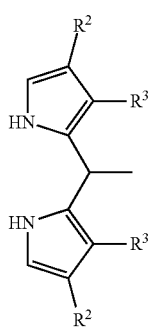

(C)

wherein $R^2$ and $R^3$ are as given above,

L is a linker group or covalent bond; and

D is a group of the formula:

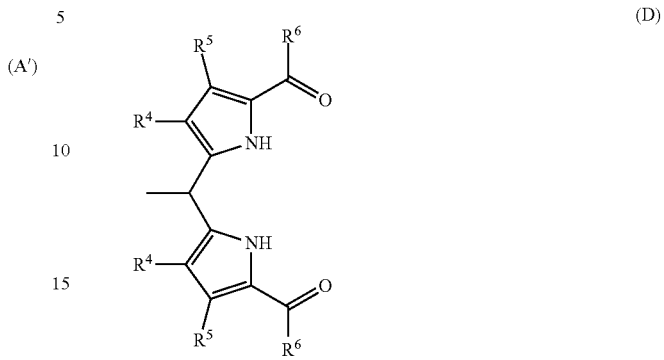

(D)

wherein $R^4$, $R^5$, and $R^6$ are as given above.

Methods described herein are sometimes described as a series of steps for the purpose of clarity of presentation, but it will be understood that embodiments of the present invention includes each of these steps when practiced independently, or as any subcombination thereof. Likewise, compounds described herein are sometimes described with the same substituent (A, B, C, D, E, F, L, $R^1$, $R^2$, $R^3$, $R^4$, $R^5$, $R^6$, etc.) for clarity, but it will be understood that each of these substituents on a compound may be the same or different depending upon the selection of intermediates and reagents.

Metalation, Linking Groups, and Further Substitutions.

"M" above represents a metal or is absent (e.g., is a pair of hydrogen atoms). Porphyrinic compounds as described above may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II), Ni(II), and Au(III). Where the metal is trivalent or tetravalent a counterion is included as necessary in accordance with known techniques.

Linking Groups for Conjugates.

Linking groups are included in compounds of the invention to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R" is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc., acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-iminobiotin, etc. Linking groups such as the foregoing are known and described in U.S. Pat. Nos. 6,728,129; 6,657,884; 6,212,093; and 6,208,553.

Conjugates.

Other groups can be attached to the active compounds to form a conjugate by means of a linking group to tune or adjust the solubility properties of the active compounds, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the active compound or attached by means of an intervening group such as a hydrophilic group, depending upon the particular linking group employed (as noted above).

Hydrophilic Groups.

Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

Surface Attachment Groups.

As noted above, compounds of the invention can be substituted with a surface attachment group, which may be in protected or unprotected form. A surface attachment group may be a reactive group coupled directly to the active compound, or coupled to the active compound by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl)phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl)phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl, 2-tellurylethyl, 3-tellurylpropyl, 2-(4-tellurylphenyl)ethynyl, 4-(2-(4-tellurylphenyl)ethynyl)phenyl, 4-tellurylmethylphenyl, 4-(2-tellurylethyl)phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl)methyl, 2-(dihydroxyphosphoryl)ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl)methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-[(hydroxy(mercapto)phosphoryl)phenyl]ethynyl, 4-[2-[4-(hydroxy(mercapto)phosphoryl)phenyl]ethynyl]phenyl, 4-(hydroxy(mercapto)phosphoryl)methyl]phenyl, 4-[2-(hydroxy(mercapto)phosphoryl)ethyl]phenyl, 4-[2-[4-(hydroxy(mercapto)phosphoryl)methylphenyl]ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl, 4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers can be employed [Nikitin, K. Chem. Commun. 2003, 282-283; Hu, J.; Mattern, D. L. J. Org. Chem. 2000, 65, 2277-2281; Yao, Y.; Tour, J. M. J. Org. Chem. 1999, 64, 1968-1971; Fox, M. A. et al. Langmuir, 1998, 14, 816-820; Galoppini, E.; Guo, W. J. Am. Chem. Soc. 2001, 123, 4342-4343; Deng, X. et al. J. Org. Chem. 2002, 67, 5279-5283; Hector Jr., L. G. et al. Surface Science, 2001, 494, 1-20; Whitesell, J. K.; Chang, H. K. Science, 1993, 261, 73-76; Galoppini, E. et al. J. Am. Chem. Soc. 2002, 67, 7801-7811; Siiman, O. et al. Bioconjugate Chem. 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl, 4-{1,1,1-tris[4-(dihydroxyphosphoryl)phenyl]methyl}phenyl,
1,1,1-tris[4-dihydroxyphosphorylmethyl)phenyl]methyl, and
4-{1,1,1-tris[4-(dihydroxyphosphorylmethyl)phenyl]methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl, Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc., Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc., Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[2-(selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

4. Utility.

The porphyrin rod compounds of the invention are useful, among other things, as light harvesting rods when immobilized or coupled to a substrate to produce light harvesting arrays, and solar cells, as described for example in U.S. Pat. No. 6,407,330 to Lindsey et al. or U.S. Pat. No. 6,420,648 to Lindsey. The porphyrin rod compounds of the invention are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. Individual porphyrinic macrocycles within the rods may comprise a member of a sandwich coordination compound in the information storage molecule, such as described in U.S. Pat. No. 6,212,093 to Li et al. or U.S. Pat. No. 6,451,942 to Li et al. The porphyrin rod compounds are also useful as active agents in photodynamic therapy, particularly where they include one or more linking group, bioconjugatable group, or targeting group, in combination with one or more water soluble group.

The present invention is explained in greater detail in the following non-limiting Examples.

EXAMPLES

For applications in the synthesis of porphyrinic precursors, an ideal α-pyrrole protecting group would afford the following features: (1) mask the α-carbon toward electrophilic aromatic substitution, (2) direct electrophilic aromatic substitution to the pyrrole 5-position without deactivation of the pyrrole ring, (3) afford stability toward acidic conditions, (4) yield a crystalline product, and (5) undergo traceless cleavage under nonacidic conditions. In contemplating candidates for protection of the α-pyrrolic position, we considered the alkylthio moiety. In this regard, Muchowski and co-workers demonstrated that a 2-alkylthiopyrrole undergoes acylation selectively at the 5-position (Franco, F. et al., *J. Org. Chem.* 1982, 47, 1682-1688). Thioethers also have been employed as traceless linkers in solid-phase chemistry (Sucholeiki, I. *Tetrahedron Lett.* 1994, 35, 7307-7310; Gayo, L. M.; Suto, M. *J. Tetrahedron Lett.* 1997, 38, 211-214; Krchnák, V.; Holladay, M. W. *Chem. Rev.* 2002, 102, 2604-2624; Rombouts, F. J. R. et al., *J. Comb. Chem.* 2005, 7, 589-598).

In this example, we describe the use of the alkylthio unit as a traceless α-pyrrole protecting group. We have screened acid catalysts and characterized the kinetics of electrophilic aromatic substitution of 2-substituted pyrroles. Our study includes the development of a mild, solventless, and stoichiometric synthesis of β-unsubstituted dipyrromethanes bearing different substituents at the mesoposition. Selective oxidation of the 1,9-bis(RS)-dipyrromethanes at the dipyrromethane unit or the sulfur moieties has been established. This work provides the foundation for the use of the alkylthio unit in pyrrole and porphyrin chemistry, masking the pyrrolic 2-position and activating the pyrrolic unit toward electrophilic substitution at the 5-position.

Results and Discussion

1. Syntheses of 2-(RS)Pyrroles.

We sought to prepare pyrrole derivatives bearing a series of α-RS groups, where R=methyl, ethyl, n-decyl, and phenyl groups. Several routes have been reported for the synthesis of 2-(RS)pyrroles lacking any other substituents, though none have been used to prepare an extensive set of homologues. The routes consist of (1) treatment of pyrrole with a dialkyl disulfide in the presence of sulfuric acid (Takeuchi, H.; Hyama, T. *Jpn. Kokai Tokkyo Koho* 1996, JP 08245558), (2) reaction of 2-thiocyanatopyrrole with a Grignard reagent (Campiani, G. et al., *J. Med. Chem.* 1998, 41, 3763-3772; Yadav, J. S. et al., *Tetrahedron Lett.* 2004, 45, 2951-2954), (3) cyclization of allyl isothiocyanate to give the pyrrole-2-thiolate followed by reaction with an alkyl halide (Klyba, L. V et al., *Russ. J. Gen. Chem.* 1999, 69 1885-1890), and (4) alkylation of pyrrole with an alkylsulfanyl chloride (Thompson, A. et al., *J. Org. Chem.* 2005, 70, 3753-3756; Leong, T. S.; Peach, M. E. *J. Fluorine Chem.* 1975, 5, 545-558; Haas, A.; Niemann, U. *Chem. Ber.* 1977, 110, 67-77; Silvestri, R. et al., *Synth. Commun.* 1994, 24, 2685-2695).6,13 We explored the first two methods.

Scheme 7

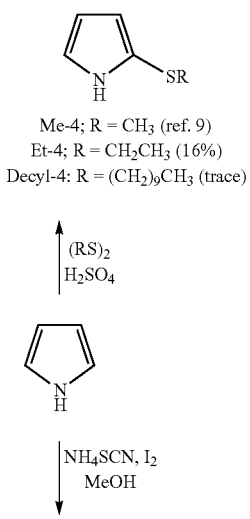

Me-4; R = CH₃ (ref. 9)
Et-4; R = CH₂CH₃ (16%)
Decyl-4: R = (CH₂)₉CH₃ (trace)

↑ (RS)₂
H₂SO₄

↓ NH₄SCN, I₂
MeOH

-continued

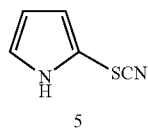

5

↓ RMgBr

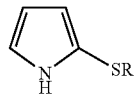

Et-4;
R = CH₂CH₃
(67%)

Ph-4; R =

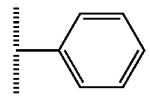

Decyl-4;
R = (CH₂)₉CH₃
(92%)

2-(Methylthio)pyrrole (Me-4) has been prepared by treatment of pyrrole with dimethyl disulfide in sulfuric acid,9 but our attempts to extend this method to the ethyl and n-decyl analogues afforded compounds Et-4 and Decyl-4 in low yield (Scheme 7).

The phenyl analogue Ph-4 has been prepared by reaction of 2-thiocyanatopyrrole (5)11 with phenylmagnesium bromide.10 2-Thiocyanatopyrrole (5), which is readily prepared by reaction of pyrrole, ammonium thiocyanate, and iodine in methanol, proved to be a versatile substrate. Thus, reaction of 5 with ethyl or n-decylmagnesium bromide afforded Et-4 or Decyl-4 in 67 or 92% yield, respectively.

3. Synthesis of Dipyrromethanes.

A. Condensation Yielding 1,9-Bis(RS)dipyrromethanes.

The condensation of Me-4 and benzaldehyde (0.25 M) was performed in CH₂Cl₂ containing TFA (0.1 M) at room temperature, leading to dipyrromethane Me-1a in 56% yield (Scheme 8).

Scheme 8

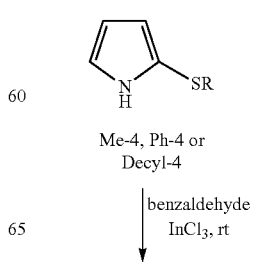

Me-4, Ph-4 or
Decyl-4

↓ benzaldehyde
InCl₃, rt

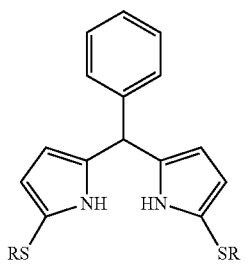

Me-1a; R = CH₃ (56% or 47%)

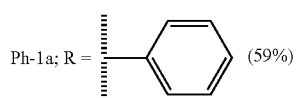

Ph-1a; R = (59%)

Decyl-1a; R = (CH₂)₉CH₃ (65%)

The same reaction in the absence of $CH_2Cl_2$ (solventless) afforded Me-1a in 47% yield. In both cases, only 2.2 equiv of Me-4 was employed, rather than a 25-100-fold excess as in the one-flask synthesis of dipyrromethanes from pyrrole and an aldehyde. The condensation of pyrrole and benzaldehyde typically affords 5-phenyldipyrromethane (1), N-confused 5-phenyldipyrromethane (2), and 5,10-diphenyltripyrrane (3). To assess the cleanliness of the reaction yielding Me-1a, each fraction obtained from column chromatography was analyzed by gas chromatography (GC), gas chromatography mass spectrometry (GC-MS), and $^1$H NMR spectroscopy. GC and GC-MS analyses showed two dominant peaks ($t_R$=19.3 and 19.6 min) that gave the same molecule ion peak (m/z=312); the former was due to dipyrromethane Me-1a, and the latter was due to a putative N-confused dipyrromethane byproduct. A similar chromatogram was observed in the condensation of pyrrole and benzaldehyde (Laha, J. K. et al., Org. Process Res. Dev. 2003, 7, 799-812). No tripyrrane species were observed. This demonstrated the stability of the methylthio protecting group toward the dipyrromethane forming reaction conditions.

The effects of TFA or a mild Lewis acid ($InCl_3$, $MgBr_2$, $Yb(OTf)_3$, or $Sc(OTf)_3$) on the reaction course in the solventless synthesis were examined. The cleanliness of the reaction was determined quantitatively by the ratio of the dipyrromethane Me-1a and the byproducts (detectable by GC analysis) and qualitatively by the darkness of the reaction mixture. The darkening of the reaction mixture signals the formation of the materials that decrease the yield and complicate the purification (such materials are difficult to quantitate by GC). The results are summarized in Table 2.

TABLE 2

Acid Screening Experiments for the Condensation of 2-(Methylthio)pyrrole (Me-4) and Benzaldehyde[a]

| acid | product/N-confused byproduct ratio[b] | darkness[c] |
|---|---|---|
| TFA | 3.3:1 | brown |
| $InCl_3$ | 6.1:1 | yellow |
| $MgBr_2$[d] | 5.9:1 | orange |
| $Sc(OTf)_3$ | 3.4:1 | orange |
| $Yb(OTf)_3$ | 4.4:1 | light yellow |

[a]Condensations (solventless) were performed with a 2:1:0.1 ratio of Me-4/benzaldehyde/acid at room temperature for 1 h.
[b]Only the peaks of Me-1a ($t_R$ = 19.3 min) and the putative N-confused byproduct ($t_R$ = 19.6 min) are considered; the peak assigned to 2-benzyl-5-(methylthio)pyrrole ($t_R$ = ~13.2 mm) was observed in all cases but not taken into consideration.
[c]Relative darkening of the reaction mixture after quenching with base.
[d]The reaction time was 16 h.

Considering all factors, $InCl_3$ afforded the best results with dipyrromethane Me-1a and was chosen as the catalyst for further studies.

The conditions using $InCl_3$ were applied with other 2-(RS) pyrroles in an effort to find substrates that afford an increase in the ratio of dipyrromethane/N-confused byproduct and also limit reliance on extensive chromatography for purification. The reaction mixture obtained from Ph-4 contained Ph-1a and no detectable quantity of N-confused byproduct, whereas that of Decyl-4 gave Decyl-1a and the N-confused byproduct in ≥20:1 ratio. The $^1$H NMR analysis showed the remaining starting material, Ph-4 or Decyl-4, in such reaction mixtures at the level of ~25 or ~5%, respectively. Attempts to separate each dipyrromethane, Ph-1a or Decyl-1a, by recrystallization of the reaction mixture were unsuccessful. Purification by passage over a short chromatographic column gave Ph-1a or Decyl-1a in 59 or 65% yield, respectively.

B. Desulfurization of 1,9-Bis(RS)Dipyrromethanes.

Carbon-sulfur bond cleavage can be achieved by desulfurization using a variety of metallic or organometallic reagents, of which Raney nickel has been used the most frequently (Pettit, G. R.; van Tamelen, E. E. Org. React. 1962, 12, 356-529; Hauptmann, H.; Walter, W. F. Chem. Rev. 1962, 62, 347-404.). Accordingly, removal of the methylthio units from dipyrromethane Me-1a was carried out by reduction with Raney nickel in refluxing EtOH. The workup procedure requires filtration through a silica pad to remove polar components and the remaining Raney nickel. The deprotected product 1a was obtained in 97% yield. Application of the same conditions to Ph-1a afforded an incomplete reaction and the formation of several pyrrolic byproducts. This observation was consistent with Brückner's report, wherein the formation of coupling byproducts occurred in the reductive desulfurization of di-2-pyrrolylthione with Raney nickel (Brückner, C. et al., J. Porphyrins Phthalocyanines 1998, 2, 455-465). In the case of Decyl-1a, Raney-nickel deprotection afforded 1a in 69% yield. The use of other reagents (e.g., nickel boride generated in situ from $NiCl_2$ and $NaBH_4$) did not afford better results.

C. Scope of Application.

The synthesis of dipyrromethanes bearing diverse meso-substituents was examined using the solventless synthesis with 2-(n-decylthio) pyrrole followed by Raney-nickel mediated desulfurization of the resulting dipyrromethane (Scheme 9).

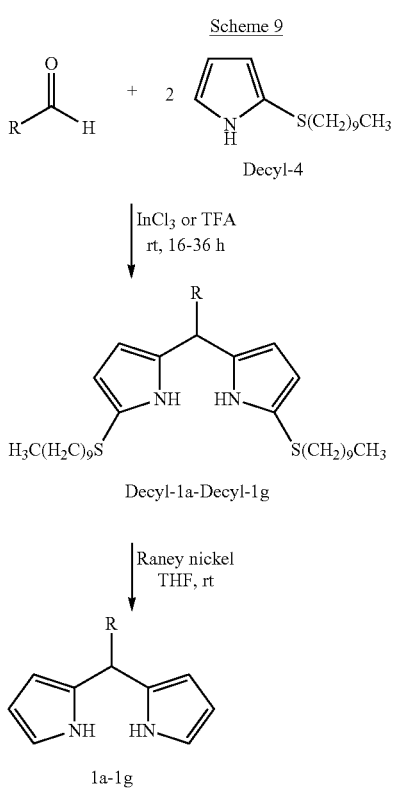

Scheme 9

Each of the target dipyrromethanes (1a (Wilson, R. M.; Hengge, A. *J. Org. Chem.* 1987, 52, 2699-270), 1b (Chong, R. et al., *Aust. J. Chem.* 1969, 22, 229-238), 1c (Lee, C. H.; Lindsey, J. S. *Tetrahedron* 1994, 50, 11427-11440), 1d (Boyle, R. W. et al., *Synlett* 1994, 939-940.), 1e (Lee, C.-H.; Kim, G.-Y. *Bull. Korean Chem. Soc.* 1996, 17, 215-217), 1f (Hammel, D. et al., *Adv. Mater.* 1992, 4 737-739), and 1g (Thamyongkit, P. et al., *J. Org, Chem.* 2004, 69, 3700-3710)) is known, and 1a-f and 1g have been prepared recently by the solventless synthesis method using pyrrole in large excess (typically 100-fold). The solventless condensation herein was carried out initially using a 2:1:0.1 ratio of Decyl-4/aldehyde/ InCl$_3$ at room temperature for 2 h. However, $^1$H NMR analysis of the reaction mixtures showed ~5% incompletion; hence, the ratio was increased to 2.2:1:0.2 and the reaction time was lengthened to 16 h. This slight modification resulted in complete consumption of the aldehydes. Attempts to use molecular sieves to remove the large quantity of water generated (~1.8 M) were unsuccessful. The application of these conditions generally gave good results. However, the swallowtail aldehyde 7-formyltridecane (Kato, M. et al., *Chem. Pharm. Bull.* 1997, 45, 1767-1776) reacted sluggishly and required 36 h for completion. Mesitaldehyde reacted smoothly upon use of TFA instead of InCl$_3$.

A simple method for the removal of InCl$_3$ entails precipitation upon addition of powdered NaOH, but traces of base deactivate Raney nickel (Grundmann, C.; Kober, E. *J. Org. Chem.* 1956, 21, 641-643). To achieve a streamlined procedure for condensation/desulfurization, the crude dipyrromethane reaction mixture was treated with hexanes, causing precipitation of InCl$_3$ while keeping the 1,9-bis(n-decylthio)dipyrromethane in solution. The sole exception occurred in the synthesis of dipyrromethane 1c where TFA catalysis was employed, whereupon the reaction mixture was neutralized by 0.1 N aqueous NaOH. The resulting crude residue directly underwent hydrodesulfurization with Raney-nickel slurry in THF at room temperature for 1-2 h. The standard workup included removal of Raney nickel by filtration followed by silica pad filtration or flash column chromatography. The yield of each dipyrromethane ranged from 38 to 66% (Table 3).

TABLE 3

Synthesis of Dipyrromethanes[a]

| Product | Meso-substituent | % Yield |
|---|---|---|
| 1a | ![phenyl] | 66 |
| 1b | H | 48 |
| 1c[b] | ![mesityl] | 66 |
| 1d | ![pentafluorophenyl] | 58 |
| 1e | ![4-methoxyphenyl] | 38 |
| 1f[c] | ![alkyl chain] | 53 |
| 1g[c,d] | ![swallowtail] | 63 |

[a]The condensations were carried out using a molar ratio of 2-(n-decylthio)pyrrole/aldehyde/ InCl$_3$ of 2.2:1.0:0.2 for 16 h at room temperature in the absence of any solvent. InCl$_3$ was removed by precipitation with hexanes. The crude product was desulfurized with Raney nickel at room temperature. The solid dipyrromethane product was isolated by precipitation.
[b]TFA (0.23 mol equiv) was employed in place of InCl$_3$; the condensation was carried out for 1.75 h, and the condensation reaction mixture was worked up by aqueous-organic extraction.
[c]Column chromatography afforded the product as an oil.
[d]The condensation was carried out for 36 h.

4. Additional Transformations.
   A. Oxidation Processes.

Dipyrromethanes typically undergo oxidation to give the corresponding dipyrrin, which can be a useful transformation in the preparation of porphyrin precursors. The 1,9-bis(RS) dipyrromethanes differ from more simple dipyrromethanes because they have two sites of reactivity toward oxidants, the dipyrromethane motif and the two thioethers. Treatment of the protected dipyrromethane Me-1a with DDQ gave the corresponding dipyrrin Me-6a in 60% yield (eq 4).

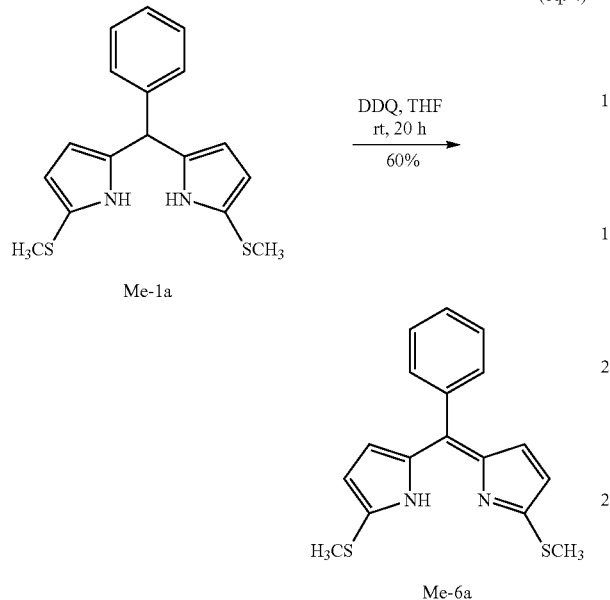

Me-1a

Me-6a (eq. 4)

Treatment of dipyrrin Me-6a with zinc acetate did not afford the corresponding bis(dipyrrinato)zinc complex, unlike dipyrromethanes lacking 1,9-substituents (Yu, L. et al., *Inorg. Chem.* 2003, 42, 6629-6647). Oxidation of the alkylthio group provides an alternative to the use of Raney nickel for carbon-sulfur cleavage. Indeed, a 2-(methylthio)pyrrole was converted to the corresponding sulfone using m-CPBA (Antonio, Y. et al., *Can. J. Chem.* 1994, 72, 15-22), and reductive desulfonation of pyrrolic compounds has been achieved with Bu$_3$SnH (photochemically) or with Na(Hg) and Na$_2$HPO$_4$ in EtOH (Pelkey, E. T. et al., *Tetrahedron Lett.* 1999, 40, 7615-7619). We found that 2-(n-decylthio)pyrrole (Decyl-4) was converted with m-CPBA to the corresponding 2-(n-decylsulfonyl)pyrrole in 69% yield. Thus, crude dipyrromethane reaction mixtures, prepared by the condensation of benzaldehyde and Me-4, Ph-4, or Decyl-4 via the solventless approach, were subjected to oxidation with m-CPBA. In two cases examined in detail (reaction of Ph-4 or Decyl-4), the corresponding bis(sulfone) was isolated in ~75% yield and at least 70% purity but proved difficult to purify to homogeneity. To facilitate isolation of the intermediate sulfones prior to desulfonation, we explored the use of tin complexation (Tamaru, S.-I. et al., *J. Org. Chem.* 2004, 69, 765-777), which afforded excellent results with the structurally similar 1,9-diacyldipyrromethanes. Tin complexation was carried out with Bu$_2$SnCl$_2$ in the presence of TEA. After filtration through a silica pad, Me-7a or Decyl-7a was isolated as a viscous oil in 5 or 9% yield, respectively. Ph-7a was obtained as platelike crystals in 21% yield upon recrystallization. The low overall yields likely stem from inefficient tin complexation. The X-ray crystal structure of tin complex Ph-7a shows one O atom of each sulfonyl group coordinated with the Sn atom, resulting in slight elongation of the S=O bond. The superior yield of Raney-nickel desulfurization made this the method of choice for deprotection.

B. Stepwise Synthesis of Dipyrromethanes.

The presence of the 2-RS substituent opens the possibility of a stepwise synthesis of dipyrromethanes. Thus, pyrrole Me-4 was acylated by N,N-dimethylbenzamide in the presence of phosphorus oxychloride following an established procedure noted above to obtain 5-benzoyl-2-(methylthio)-pyrrole (Me-8a) (Scheme 10). NaBH$_4$ reduction of Me-8a led to the corresponding carbinol derivative. Condensation of the carbinol derivative with a stoichiometric amount of pyrrole Me-4 in the presence of InCl$_3$ (0.1 equiv) gave Me-1a in 45% yield. This route illustrates the potential for exploitation of the 2-alkylthio group in stepwise syntheses of pyrromethane compounds.

Scheme 10

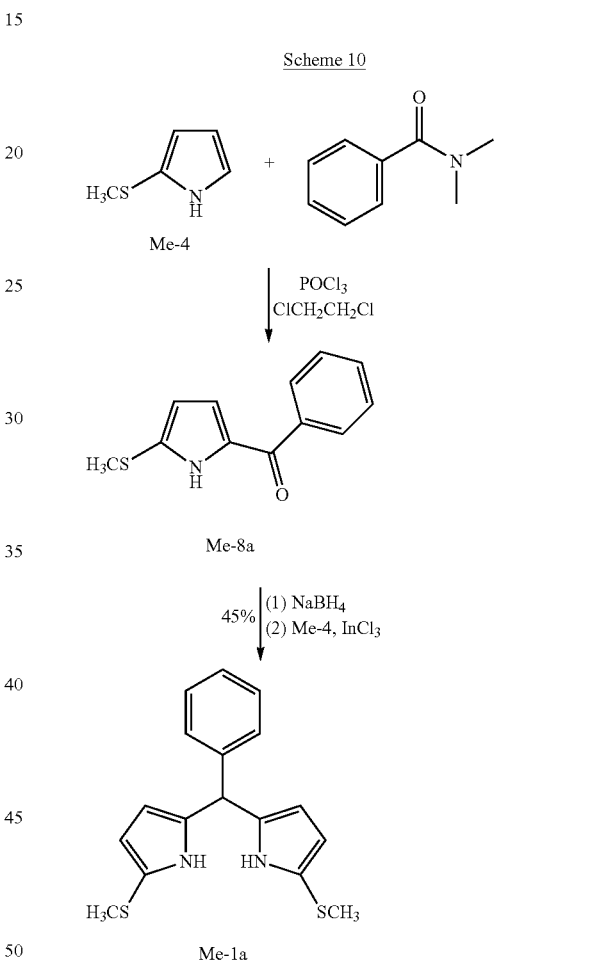

Experimental Section
General.

All $^1$H NMR (400 MHz) and $^{13}$C NMR (100 MHz) spectra were collected in CDCl$_3$ unless noted otherwise. Absorption spectra were collected in toluene at room temperature. Mass spectra of porphyrins were obtained via laser desorption mass spectrometry (LD-MS) without a matrix (Srinivasan, N. et al., *J. Porphyrins Phthalocyanines* 1999, 3, 283-291; Fenyo, D. et al., *J. Porphyrins Phthalocyanines* 1997, 1, 93-99), and by high-resolution fast atom bombardment mass spectrometry (FAB-MS) using a matrix of nitrobenzyl alcohol and polyethylene glycol. Melting points are uncorrected. Silica gel (40 µm average particle size) was used for column chromatography. The Raney nickel 2800 slurry in water was washed with EtOH by addition-decantation and then used as a slurry in EtOH. In the scalable synthesis of dipyrromethanes, the Raney nickel 2800 slurry in water was washed with THF (with use of a Buchner funnel) and then used as a slurry in THF. The commercial sample of m-CPBA contains a maximum of 77% m-CPBA. THF was freshly distilled from sodium as required. Toluene was distilled from $CaH_2$. $CHCl_3$ was stabilized with 0.8% EtOH.

Noncommercial Compounds.

2-(Methylthio)pyrrole (Me-4) (Takeuchi, H.; Hyama, T. *Jpn. Kokai Tokkyo Koho* 1996, JP 08245558), 2-(phenylthio) pyrrole (Ph-4) (Campiani, G. et al., *J. Med. Chem.*, 1998, 41, 3763-3772), 2-thiocyanatopyrrole (5) (Yadav, J. S. et al., *Tetrahedron Lett.* 2004, 45, 2951-2954), 5-benzoyl-2-(methylthio)pyrrole (Me-8a)(Franco, F. et al., *J. Org. Chem.* 1982, 47, 1682-1688) and 7-formyltridecane (Kato, M. et al., *Chem. Pharm. Bull.* 1997, 45, 1767-1776) were obtained by literature procedures. The first synthesis of each dipyrromethane was as follows: 1a (Wilson, R. M.; Hengge, A. *J. Org. Chem.* 1987, 52, 2699-2707), 1b (Chong, R. et al., *Aust. J. Chem.* 1969, 22, 229-238), 1c (Lee, C.-H.; Lindsey, J. S. *Tetrahedron* 1994, 50, 11427-11440), 1d (Boyle, R. W. et al., *Synlett* 1994, 939-940), 1e (Lee, C.-H.; Kim, J.-Y. *Bull. Korean Chem. Soc.* 1996, 17, 215-217), 1f (Hammel, D. et al., *Adv. Mater.* 1992, 4, 737-739), 1g (Thamyongkit, P. et al., *J. Org. Chem.* 2004, 69, 3700-3710). Each of 1a-f also has been prepared recently by a solventless synthesis method (Laha, J. K. et al., *Org. Process Res. Dev.* 2003, 7, 799-812). 2-(Ethylthio)pyrrole (Et-4) (Klyba, L. V. et al., *Russ. J. Gen. Chem.* 1999, 69, 1885-1890) is a known compound but was prepared by an alternative route (see below).

1,9-Bis(phenylthio)-5-phenyldipyrromethane (Ph-1a)

Following the solventless preparation described for Me-1a, benzaldehyde (42.6 mg, 401 µmol) was treated with Ph-4 (141 mg, 805 µmol) in the presence of $InCl_3$ (9.0 mg, 41 µmol) at room temperature for 16 h. Workup and subsequent column chromatography [silica, hexanes/ethyl acetate (8:1)] afforded a yellow viscous oil (103 mg, 59%), which solidified after 24 h at −15° C.: mp 81° C.; $^1$H NMR (THF-$d_8$) δ 5.44 (s, 1H), 5.80-5.81 (m, 2H), 6.33-6.35 (m, 2H), 6.97-7.03 (m, 6H), 7.13-7.20 (m, 7H), 7.25-7.29 (m, 2H), 10.52 (br s, 2H); $^{13}$C NMR (THF-$d_8$) δ 45.4, 110.2, 115.2, 119.1, 125.6, 126.1, 127.4, 129.0, 129.4, 129.5, 138.7, 141.6, 143.4; FAB-MS obsd 438.1211, calcd 438.1224 ($C_{27}H_{22}N_2S_2$).

1,9-Bis(n-decylthio)-5-phenyldipyrromethane (Decyl-1a)

A solution of Decyl-4 (3.35 g, 14.0 mmol) and benzaldehyde (0.707 mL, 7.00 mmol) at room temperature was treated with $InCl_3$ (154 mg, 0.70 mmol). The resulting mixture was stirred at room temperature for 2 h. After complete consumption of starting material as indicated by TLC, the reaction mixture was diluted with toluene and washed with water. The organic layer was dried ($Na_2SO_4$), concentrated and chromatographed [silica, hexanes/$CH_2Cl_2$ (7:3)] to afford a viscous liquid, wherein a trace of $CH_2Cl_2$ was observed by NMR analysis (~2.58 g, ~65%): $^1$H NMR δ 0.86-0.90 (m, 6H), 1.25-1.36 (m, 28H), 1.46-1.56 (m, 4H), 2.56-2.60 (m, 4H), 5.38 (s, 1H), 5.86-5.88 (m, 2H), 6.27-6.28 (m, 2H), 7.17-7.20 (m, 2H), 7.27-7.36 (m, 3H), 7.88 (br s, 2H); $^{13}$C NMR δ 14.3, 22.8, 28.6, 29.4, 29.4, 29.7, 29.7, 30.0, 32.0, 38.1, 44.4, 109.2, 116.8, 119.2, 127.4, 128.4, 128.9, 134.6, 141.2; Anal. Calcd for $C_{35}H_{54}N_2S_2$: C, 74.15; H, 9.60; N, 4.94. Found: C, 74.16; H, 9.65; N, 4.94.

2-(Ethylthio)pyrrole) (Et-4) was synthesized by two different methods as described below:

Method 1.

Following a literature procedure as noted above, a solution of 7 (2.00 g, 16.1 mmol) in THF (8 mL) was added dropwise to a solution of ethylmagnesium bromide (32.0 mL, 32 mmol, 1.0 M solution in THF) in dry THF (72.0 mL) at 0° C. After stirring for 2 h at 0° C., the reaction mixture was poured on ice and extracted with ethyl acetate. The organic layer was washed with saturated aqueous $NH_4Cl$, dried ($Na_2SO_4$), and concentrated. The crude product was chromatographed [silica, hexanes/$CHCl_3$ (1:2)] to afford a viscous liquid (1.37 g, 67%): $^1$H NMR δ 1.22 (t, J=7.3 Hz, 3H), 2.67 (q, J=7.3 Hz, 2H), 6.21-6.24 (m, 1H), 6.38-6.40 (m, 1H), 6.83-6.85 (m, 1H), 8.25 (br s, 1H); $^{13}$C NMR (75 MHz) δ 15.5, 32.1, 110.2, 116.9, 119.4, 120.6; Anal. Calcd for $C_6H_9NS$: C, 56.65; H, 7.13; N, 11.01. Found: C, 56.85; H, 7.24; N, 10.92.

Method 2.

Following a literature procedure as noted above, a solution of diethyl disulfide (6.11 g, 50.0 mmol) and pyrrole (10.4 mL, 150 mmol) was added dropwise to concentrated $H_2SO_4$ (20.0 mL, 375 mmol) at room temperature over a period of 37 min. The reaction mixture was stirred for 3 h 40 min. The reaction mixture was poured on ice and extracted with $CH_2Cl_2$. The organic layer was dried ($Na_2SO_4$), concentrated and chromatographed [silica, hexanes/$CH_2Cl_2$ (1:1)] to afford a viscous liquid (1.06 g, 16%). Characterization data (mp, $^1$H NMR, $^{13}$C NMR) are consistent with those described above.

2-(n-Decylthio)pyrrole (Decyl-4)

Following a procedure for Et-4 (Method 1), a solution of 5 (6.00 g, 48.3 mmol) in THF (10 mL) was added dropwise to a solution of n-decylmagnesium bromide (96.6 mL, 97 mmol, 1.0 M solution in $Et_2O$) in dry THF (220 mL) at 0° C. After stirring for 40 min at 0° C., the yellow reaction mixture was poured on ice and extracted with ethyl acetate (128 mL). The organic layer was washed with saturated aqueous $NH_4Cl$ (100 mL), dried ($Na_2SO_4$), and concentrated. The resulting residue was chromatographed [silica, hexanes/$CHCl_3$ (1:3), ~350 mL, 4 cm dia×25 cm in height] to afford a viscous liquid (10.7 g, 92%): $^1$H NMR δ 0.88 (t, J=6.8 Hz, 3H), 1.25-1.39 (m, 14H), 1.50-1.58 (m, 2H), 2.63 (t, J=7.2 Hz, 2H), 6.20-6.23 (m, 1H), 6.35-6.38 (m, 1H), 6.82-6.84 (m, 1H), 8.20 (br s, 1H); $^{13}$C NMR δ 14.3, 22.9, 28.7, 29.4, 29.5 29.70, 29.72, 30.1, 32.1, 38.1, 110.1, 116.5, 119.7, 120.3; FAB-MS: obsd 239.1686, calcd 239.1708 ($C_{14}H_{25}NS$). Anal. Calcd for $C_{14}H_{25}NS$: C, 70.23; H, 10.52; N, 5.85. Found: C, 70.42; H, 10.54; N, 5.89.

Reductive Desulfurization of Me-1a to Obtain 5-Phenyldipyrromethane (1a).

By Raney Nickel.

Raney nickel (~500 mg, slurry in EtOH) with additional EtOH (5 mL) was treated with Me-1a (50.0 mg, 159 µmol) at room temperature and the reaction mixture was heated to reflux. After 30 min, TLC showed the complete consumption of Me-1a. The reaction mixture was filtered and washed with diethyl ether. Note that Raney nickel must be handled under a solvent at all times. The filtrate was concentrated to dryness. The resulting residue was dissolved in $CH_2Cl_2$. The solution was filtered through a silica pad ($CH_2Cl_2$). The eluant was concentrated, affording a white solid (34 mg, 97%): mp 100° C. (lit. 100.2-101.1° C.); $^1$H NMR (THF-$d_8$) δ 5.48 (s, 1H), 5.95 (s, 2H), 6.18-6.21 (m, 2H), 6.70 (s, 2H), 7.23-7.38 (m, 5H), 7.89 (br s, 2H); $^{13}$C NMR (THF-$d_8$) δ 43.9, 107.2, 108.4, 117.2, 126.9, 128.4, 128.6, 132.5, 142.0; LD-MS obsd 732.6. Anal. Calcd for $C_{15}H_{14}N_2$: C, 81.05; H, 6.35; N, 12.60. Found: C, 81.07; H, 6.34; N, 12.54.

Reductive Desulfurization of Decyl-1a to Obtain 5-Phenyldipyrromethane (1a).

The cleavage of the n-decylthio unit in Decyl-1a was accomplished by two different methods as described below:

By Raney Nickel.

Following the procedure described for Me-1a, a mixture of Decyl-1a (1.00 g, 1.76 mmol) in EtOH (20 mL, 95%) was treated with a freshly prepared slurry of Raney nickel (~7.00 g, slurry in EtOH) at room temperature. The mixture was refluxed for 45 min. Upon complete consumption of starting material as indicated by TLC, the reaction mixture was filtered through Celite (~1 cm) and the filtered residue was washed with EtOH (95%). The filtrate was concentrated and chromatographed (silica, $CH_2Cl_2$), affording an off-white solid (272 mg, 69%). Characterization data (mp, $^1H$ NMR, $^{13}C$ NMR, elemental analysis) were consistent with those described above.

By $NiCl_2/NaBH_4$.

Following the procedure described for Me-1a, a mixture of Decyl-1a (1.00 g, 1.76 mmol) in dry MeOH (8.00 mL) was treated with $NiCl_2$ (2.73 g, 21.1 mmol) followed by the addition of $NaBH_4$ (2.39 g, 63.3 mmol) at room temperature. A small amount of dry MeOH (8.00 mL) was added to solubilize residual material on the wall of the flask. The mixture was stirred for 15 min. Formation of nickel boride was indicated by rapid formation of a black precipitate with the evolution of gas. Upon complete consumption of starting material, the reaction mixture was filtered through Celite (~1 cm). The filtered black residue was washed with MeOH. The combined washings were treated with water and extracted with toluene. The organic phase was dried ($Na_2SO_4$), concentrated and chromatographed (silica, $CH_2Cl_2$) to afford a gray solid (0.197 g) containing 1a (~80% purity by NMR analysis).

Dipyrromethane (1b).

Following a general procedure described above, a sample of paraformaldehyde (0.225 mg, 7.50 mmol) and Decyl-4 (3.95 g, 16.5 mmol) was heated at 70° C. to obtained a homogeneous mixture. The mixture was treated with $InCl_3$ (0.332 g, 1.50 mmol) and stirred at room temperature for 16 h. $^1H$ NMR analysis showed the complete consumption of paraformaldehyde. The reaction mixture was worked up with hexanes/THF (2:1) and the organic extract was concentrated to dryness. The resulting crude mixture was treated with Raney nickel (30 g) in THF (5.0 mL) at room temperature for 1 h. Raney nickel was removed by filtration and washed with THF (550 mL). The filtrate was concentrated to dryness. The resulting residue was chromatographed [silica, hexanes/$CH_2Cl_2$ (2:1), 2×5 cm]. The eluant was concentrated. The resulting pale yellow solid was treated with hot hexanes/$CH_2Cl_2$ (10:1) and cooled to room temperature, affording off-white crystals (0.522 g, 48%): mp 69-70° C. (lit. 74° C.); $^1H$ NMR δ 3.96 (s, 2H), 6.05-6.10 (m, 2H), 6.15-6.20 (m, 2H), 6.60-6.68 (m, 2H), 7.74 (br s, 2H); $^{13}C$ NMR δ 26.2, 106.4, 108.3, 117.3, 129.1. Anal. Calcd for $C_9H_{10}N_2$: C, 73.94; H, 6.89; N, 19.16. Found: C, 73.75; H, 6.96; N, 18.92.

5-Mesityldipyrromethane (1c)

Following the standard procedure with slight modification, a mixture of mesitaldehyde (1.11 g, 7.50 mmol) and Decyl-4 (3.95 g, 16.5 mmol) was treated with TFA (0.133 mL, 1.72 mmol) at room temperature. After 1.75 h, $^1H$ NMR analysis showed the complete consumption of mesitaldehyde. The reaction mixture was treated with 0.1N aqueous NaOH (15 mL) and extracted with $CH_2Cl_2$ (100 mL). The organic layer was washed (water and brine), dried ($Na_2SO_4$), and concentrated to dryness. The resulting residue was treated with Raney nickel (40 g) in THF (5.0 mL) at room temperature for 2 h. The Raney nickel was removed by filtration and washed with THF (450 mL). The filtrate was concentrated to dryness. The resulting residue was passed through a pad of silica [$CH_2Cl_2$/hexanes (7:3), ~200 mL, 2×5 cm], affording a greenish solid. The greenish solid was treated with hot $CH_2Cl_2$/hexanes and filtered at room temperature to afford a white crystalline solid (900 mg, 46%). The filtrate was concentrated to dryness. The residue was treated with hexanes and the mixture was filtered to obtain additional product as a pale yellow powder (390 mg, 20%), affording an overall yield of 66%: mp 167-168° C. (lit. 166-167° C.); $^1H$ NMR (300 MHz) δ 2.07 (s, 6H), 2.29 (s, 3H), 5.94 (s, 1H), 6.01-6.04 (m, 2H), 6.17-6.20 (m, 2H), 6.65-6.69 (m, 2H), 6.86-6.89 (m, 2H), 7.94 (br s, 2H); $^{13}C$ NMR (75 MHz) δ 20.7, 20.9, 38.4, 106.6, 108.8, 116.3, 130.5, 131.4, 134.6, 136.7, 137.7; FAB-MS obsd 264.1626, calcd 264.1608.

5-(Pentafluorophenyl)dipyrromethane (1d)

Following the standard procedure, a mixture of pentafluorobenzaldehyde (1.47 g, 7.50 mmol) and Decyl-4 (3.95 g, 16.5 mmol) was treated with $InCl_3$ (0.332 g, 1.50 mmol) at room temperature. After 16 h, $^1H$ NMR analysis showed the complete consumption of pentafluorobenzaldehyde. The reaction mixture was treated with hexanes (5 mL) and filtered through a sintered glass fritted funnel. The filtrate was concentrated to dryness. The resulting residue was treated with Raney nickel (30 g) in THF (5.0 mL) at room temperature for 1 h. The Raney nickel was removed by filtration and washed with THF (150 mL). The filtrate was concentrated to dryness. The resulting residue was passed through a pad of silica [hexanes/toluene (1:2), ~200 mL, 3×2 cm], affording an off-white solid. The solid was triturated with $CH_2Cl_2$/hexanes and isolated by filtration, affording a white solid (1.36 g, 58%): mp 129-130° C.; $^1H$ NMR δ 5.91 (s, 1H), 6.02-6.04 (m, 2H), 6.16-6.19 (m, 2H), 6.74-6.75 (m, 2H), 8.17 (br s, 2H); $^{13}C$ NMR δ 33.0, 107.6, 108.6, 118.1, 128.1, resonances from the pentafluorophenyl group were not observed clearly; Anal. Calcd for $C_{15}H_9F_5N_2$: C, 57.70; H, 2.91; N, 8.97. Found: C, 57.43; H, 2.83; N, 8.78.

5-(4-Methoxyphenyl)dipyrromethane (1e)

Following the standard procedure, a mixture of anisaldehyde (1.02 g, 7.50 mmol) and Decyl-4 (3.95 g, 16.5 mmol) was treated with $InCl_3$ (0.332 g, 1.50 mmol) at room temperature. After 16 h, $^1H$ NMR analysis showed the complete consumption of anisaldehyde. The reaction mixture was treated with hexanes (5.0 mL) and filtered through a sintered glass fritted funnel. The filtrate was concentrated to dryness. The resulting residue was treated with Raney nickel (30 g) in THF (5.0 mL) at room temperature for 1.5 h. The Raney nickel was removed by filtration and washed with THF (350 mL). The filtrate was concentrated to dryness. The resulting residue was chromatographed [silica, toluene/hexanes (2:1), 1.5×4 cm], affording a pale yellow solid. The solid was heated with hexanes/$CH_2Cl_2$ (9:1) and then isolated by filtration (0.712 g, 38%): mp 96-98° C. (99° C.; Littler, B. J. et al., *J. Org. Chem.* 1999, 64, 1391-1396); $^1H$ NMR (300 MHz) δ 3.80 (s, 3H), 5.43 (s, 1H), 5.90-5.94 (m, 2H), 6.14-6.18 (m, 2H), 6.68-6.72 (m, 2H), 6.85 (d, J=8.4 Hz, 2H), 7.13 (d, J=8.4 Hz, 2H), 7.91 (br s, 2H); $^{13}C$ NMR (75 MHz) δ 43.3, 55.5, 107.2, 108.6, 114.1, 117.3, 129.6, 133.0, 134.4, 158.7; Anal. Calcd for $C_{16}H_{16}N_2$: C, 76.16; H, 6.39; N, 11.10. Found: C, 75.82; H, 6.39; N, 10.78.

5-n-Pentyldipyrromethane (1f)

Following the standard procedure, a mixture of hexanal (0.751 mg, 7.50 mmol) and Decyl-4 (3.95 g, 16.5 mmol) was treated with $InCl_3$ (0.332 g, 1.50 mmol) at room temperature. After 16 h, $^1$H NMR analysis showed the complete consumption of hexanal and the reaction mixture was treated with hexanes (5.0 mL). After filtration through a sintered glass fritted funnel, the filtrate was concentrated to dryness. The resulting residue was treated with Raney nickel (30 g) in THF (5.0 mL) at room temperature for 1 h. The Raney nickel was removed by filtration and washed with THF (150 mL). The filtrate was concentrated to dryness. The resulting residue was chromatographed [silica, hexanes/$CH_2Cl_2$ (2:1), 2×8 cm], affording a pale yellow oil (0.852 g, 53%): $^1$H NMR δ 0.86-0.89 (m, 3H), 1.27-1.35 (m, 6H), 1.92-1.97 (m, 2H), 3.98 (t, J=7.6 Hz, 1H), 6.07-6.09 (m, 2H), 6.14-6.17 (m, 2H), 6.63-6.65 (m, 2H), 7.79 (br s, 2H); $^{13}$C NMR δ 14.3, 22.8, 27.5, 32.0, 34.7, 37.9, 105.6, 108.2, 117.2, 133.9; FAB-MS obsd 216.1626, calcd 216.1617 ($C_{14}H_{20}N_2$).

5-(Tridec-7-yl)dipyrromethane (1g)

Following the standard procedure, a mixture of 7-formyltridecane (1.59 g, 7.50 mmol) and Decyl-4 (3.95 g, 16.5 mmol) was treated with $InCl_3$ (0.364 g, 1.65 mmol) at room temperature. After 36 h, NMR analysis showed the complete consumption of 7-formyltridecane. The reaction mixture was treated with hexanes (5.0 mL) and filtered through a sintered glass fritted funnel. The filtrate was concentrated to dryness. The resulting residue was treated with Raney nickel (30 g) in THF (5.0 mL) at room temperature for 1 h. The Raney nickel was removed by filtration and washed with THF (150 mL). The filtrate was concentrated to dryness. The resulting residue was chromatographed [silica, toluene/hexanes (2:1), 3×9 cm], affording pale yellow oil (1.16 g, 63%): $^1$H NMR (300 MHz) δ 0.85-0.90 (m, 6H), 1.15-1.46 (m, 20H), 1.90-2.00 (m, 1H), 4.10-4.14 (m, 1H), 6.00-6.06 (m, 2H), 6.13-6.18 (m, 2H), 6.60-6.66 (m, 2H), 7.80 (br s, 2H); $^{13}$C NMR (75 MHz) δ 14.3, 22.9, 27.7, 29.9, 31.8, 32.1, 41.0, 41.9, 106.4, 108.2, 116.8, 132.4; Anal. Calcd for $C_{22}H_{36}N_2$: C, 80.43; H, 11.04; N, 8.53. Found: C, 80.21; H, 11.27; N, 8.50.

Synthesis of 1a with Addition of Molecular Sieves 4 A as a Desiccant.

Following the standard procedure with slight modification, a mixture of benzaldehyde (0.796 g, 7.50 mmol) and Decyl-4 (3.95 g, 16.5 mmol) was treated with $InCl_3$ (0.332 g, 1.50 mmol) and molecular sieves (4 A, 0.744 g). The mixture was stirred at room temperature for 16 h. The resulting brownish mixture was treated with hexanes (5 mL), affording a brownish mixture. The $^1$H NMR spectrum of the reaction mixture showed ~12% of unreacted benzaldehyde. The mixture was filtered through a sintered glass fritted funnel and the filtered material was washed with a small amount of hexanes. The filtrate was concentrated to dryness. The resulting crude brown residue was treated with Raney nickel (30 g) in THF (5.0 mL) at room temperature for 1 h. The mixture was filtered to remove the Raney nickel and the filtered material was washed with THF (~150 mL). The filtrate was concentrated to dryness. The resulting yellow residue was filtered through a silica pad [hexanes/toluene (1:2), ~250 mL, 1.5×2 cm]. The combined fractions were concentrated to dryness. The resulting yellowish solid was heated with $CH_2Cl_2$/hexanes (1:9, 20 mL). After a few minutes, the slurry was filtered and the filtered residue was washed with hexanes (5 mL) to obtain a white crystalline solid (700 mg, 42%). The filtrate was concentrated to dryness and treated with hexanes to form a turbid mixture. The turbid mixture was filtered to obtain a second crop of product (50.0 mg, 3%). The overall yield was 45%. The characterization data (mp, $^1$H NMR, $^{13}$C NMR) were consistent with those described above.

Synthesis of 1a Using an Ethylthio α-Pyrrole Protecting Group.

Following the standard procedure, a mixture of benzaldehyde (0.796 g, 7.50 mmol) and Et-4 (2.10 g, 16.5 mmol) was treated with $InCl_3$ (0.332 g, 1.50 mmol) at room temperature. After 3.5 h, $^1$H NMR analysis showed the complete consumption of benzaldehyde. The reaction mixture was treated with hexanes (5.0 mL) and filtered through a sintered glass fritted funnel. The filtrate was concentrated to dryness. The resulting residue was treated with Raney nickel (30 g) in THF (5.0 mL) at room temperature for 2 h. Raney nickel was filtered off and washed with THF (150 mL). The filtrate was concentrated to dryness. The resulting residue was chromatographed [silica, hexanes/$CH_2Cl_2$ (1:1), 2×20 cm], affording a yellow oil containing 1a (~90% purity by $^1$H NMR analysis) and an unknown byproduct having a similar $R_f$ upon TLC analysis. The yellow oil was refluxed with hexanes (20 mL), affording a yellow solid (0.450 g, 27%, >95% purity by $^1$H NMR spectroscopy). The characterization data ($^1$H NMR, $^{13}$C NMR) were consistent with those described above.

Dibutyl[5,10-dihydro-1,9-bis(phenylsulfonyl)-5-phenyldipyrrinato]tin(IV) (Ph-7a)

Following the procedure described for tin-complex Me-7a, a mixture of pyrrole Ph-4 (500 mg, 2.85 mmol) and benzaldehyde (151 mg, 1.43 mmol) was treated with $InCl_3$ (31.6 mg, 0.143 mmol) in a minimal amount of toluene (~0.5 mL) for 24 h. After workup, one-third of the resulting crude residue was treated with m-CPBA (460 mg, 2.05 mmol) in $CH_2Cl_2$ (8.5 mL). The crude mixture was treated with $Bu_2SnCl_2$ (109 mg, 0.359 mmol) in the presence of TEA (0.150 mL, 1.08 mmol) and $CH_2Cl_2$ (3.0 mL). Filtration of the resulting mixture through a silica pad ($CH_2Cl_2$) followed by recrystallization (diethyl ether) gave colorless plate-like crystals (71 mg, 21% from pyrrole Ph-4): mp 154° C.; $^1$H NMR (THF-$d_8$) δ 0.63-0.73 (m, 6H), 0.88-1.17 (m, 4H), 1.23-1.48 (m, 4H), 1.64-1.83 (m, 4H), 5.52 (s, 1H), 6.26 (d, J=3.2 Hz, 2H), 6.89 (d, J=3.2 Hz, 2H), 6.93 (d, J=6.8 Hz, 2H), 7.11-7.19 (m, 3H), 7.50-7.60 (m, 6H), 7.78 (d, J=6.8 Hz, 4H); $^{13}$C NMR (THF-$d_8$) δ 13.81, 13.85, 26.6, 27.10, 27.13, 27.4, 27.8, 29.4, 45.8, 115.1, 118.6, 126.8, 127.3, 128.83, 128.90, 130.0, 131.5, 133.6, 144.8, 145.3, 146.0; LD-MS obsd 732.6. Anal. Calcd for $C_{35}H_{38}N_2O_4S_2Sn$: C, 57.31; H, 5.22; N, 3.82. Found: C, 57.14; H, 5.26; N, 3.81.

Dibutyl[1,9-bis(n-decylsulfonyl)-5,10-dihydro-5-phenyldipyrrinato]tin(IV) (Decyl-7a)

Following the procedure described for tin-complex Me-7a, a mixture of pyrrole Decyl-4 (563 mg, 9.42 mmol) and benzaldehyde (119 mL, 1.18 mmol) was treated with $InCl_3$ (26.1 mg, 0.118 mmol) for 2.25 h. After workup, half of the resulting crude residue was treated with m-CPBA (271 mg, 1.21 mmol) in $CH_2Cl_2$ (10 mL). The crude mixture was treated with $Bu_2SnCl_2$ (123 mg, 0.403 mmol) in the presence of TEA (0.168 mL, 1.21 mmol) and $CH_2Cl_2$ (3.0 mL). The resulting mixture was filtered through a silica pad ($CH_2Cl_2$). The eluant was concentrated to a gum, which upon washing with diethyl ether gave a pale yellow viscous oil (46 mg, 9% from pyrrole Decyl-4): $^1$H NMR (THF-d$_8$) δ 0.69-0.76 (m, 6H), 0.88-0.91 (m, 18H), 1.00-1.08 (m, 6H), 1.12-1.20 (m, 4H), 1.26-1.40 (m, 16H), 1.56-1.70 (m, 6H), 3.19 (t, J=8.0 Hz, 4H), 5.53 (s, 1H), 6.30 (d, J=3.2 Hz, 2H), 6.87 (d, J=3.2 Hz, 2H), 6.92 (d, J=7.6 Hz, 2H), 7.08-7.17 (m, 3H); $^{13}$C NMR (THF-d$_8$) δ 13.8, 14.0, 14.5, 23.6, 24.1, 24.9, 26.5, 26.9, 27.30, 27.35, 27.5, 28.0, 29.1, 29.9, 30.16, 30.29, 30.33, 30.38, 30.53, 30.69, 30.72, 30.8, 31.5, 32.91, 32.94, 43.1, 45.6, 58.2, 71.4, 114.3, 116.8, 127.0, 128.5, 128.8, 131.2, 145.1, 145.9; LD-MS obsd 860.5, calcd 861.9 ($C_{43}H_{70}N_2O_4S_2Sn$).

Synthesis of 2-(n-Decylsulfonyl)pyrrole

Following a literature procedure (Antonio, Y. et al., *Can. J. Chem.* 1994, 72, 15-22), Decyl-4 (500 mg, 2.08 mmol) in dichloromethane (3 mL) was treated with a solution of m-CPBA (1.22 g, 70% purity, 4.16 mmol) in dichloromethane (12 mL). After 1 h the reaction mixture was washed with saturated aqueous NaHCO$_3$. The organic phase was dried (Na$_2$SO$_4$) and concentrated. The crude product was chromatographed (silica, ethyl acetate) affording a brown viscous liquid (390 mg, 69%): $^1$H NMR (300 MHz, CDCl$_3$) δ 0.87 (t, J=6.3 Hz, 3H), 1.07-1.40 (m, 14H), 1.64-1.72 (m, 2H), 3.12 (t, J=7.9 Hz, 2H), 6.32-6.34 (m, 1H), 6.82-6.90, m, 1H), 6.98-7.45 (m, 1H), 9.70 (br s, 1H); $^{13}$C NMR δ 14.3, 22.9, 23.0, 28.3, 29.2, 29.42, 29.44, 29.6, 32.0, 27.4, 111.0, 115.9, 123.8, 126.0; FAB-MS obsd 272.1684, calcd 272.1673 ($C_{14}H_{25}NO_2S$); Anal. Calcd for $C_{14}H_{25}NO_2S$: C, 61.95; H, 9.28; N, 5.16. Found: C, 62.35; H, 9.37; N, 4.97.

Effect of α-Pyrrole Substituents: Kinetic Study of Deuteration.

A solution of CD$_3$COOD (600 μL, 10.5 mmol) was added to an α-substituted pyrrole (52 μmol) in an NMR tube at 20° C. Kinetic measurements were made by $^1$H NMR spectroscopy to at least 90% exchange for the protons undergoing fast exchange and to at least 60% exchange for those undergoing slow exchange.

Acid Screening Experiment.

All experiments were carried out in the absence of a solvent. Each experiment employed benzaldehyde (42.6 mg, 401 μmol), Me-4 (91.0 mg, 804 μmol), and an acid (40 μmol, 0.1 equiv relative to benzaldehyde) [TFA (3.1 μL), InCl$_3$ (8.9 mg), MgBr$_2$ (7.4 mg), Yb(OTf)$_3$ (25 mg) or Sc(OTf)$_3$ (20 mg)]. The reaction was monitored by thin-layer chromatography (TLC) analysis and stopped after the consumption of benzaldehyde was complete. In each case, the reaction was quenched by adding 0.1 N aqueous NaOH and ethyl acetate after 1 h (with the exception of the reaction using MgBr$_2$, which took 16 h). After drying and concentrating to dryness, each crude mixture was analyzed by $^1$H NMR spectroscopy and GC. $^1$H NMR spectra showed compound Me-1a as the main component and small peaks of the unreacted 2-(methylthio)pyrrole. A peak due to an N-confused byproduct could not be clearly observed. Therefore, GC analysis was employed to compare the yield and the cleanliness of the reaction. The solution for the GC analysis was prepared by diluting 5.0 mg of the crude mixture in 0.45 mL of THF.

1,9-Bis(methylthio)-5-phenyldipyrromethane (Me-1a)

Several conditions were investigated. The title compound was obtained both under solution and under solventless conditions. The preferred solventless condition was employed for the acid screening study.

Solution Synthesis.

A mixture of benzaldehyde (42.6 mg, 401 μmol, 0.25 M) and Me-4 (100 mg, 884 μmol, 2.2 equiv) in CH$_2$Cl$_2$ (1.6 mL) was degassed for 5 min at room temperature. TFA (12.0 μL, 156 μmol, 0.1 M) was added. The reaction was stopped after 30 min, when the consumption of benzaldehyde was complete (by TLC and $^1$H NMR spectroscopy). The violet reaction mixture was treated with a mixture of 0.1 N aqueous NaOH and ethyl acetate (10 mL, 1:1). The resulting orange mixture was extracted with CH$_2$Cl$_2$. The organic phase was collected, dried (Na$_2$SO$_4$), and concentrated. The crude mixture was passed through a silica column (hexanes/ethyl acetate (8:1), 2.5 cm diameter ~18 cm in height). Four fractions were obtained. The first fraction (yellow, Rf=0.50) contained unknown pyrrole derivatives (by $^1$H NMR analysis). The second fraction (colorless) consisted of unreacted Me-4 (Rf=0.45). The third fraction (Rf=0.21) contained the product (Me-1a) in the form of a viscous yellow oil (71 mg, 56%), which solidified after 24 h at −15° C. The last fraction had the same color and retention (Rf=0.21) as that of the product, but $^1$H NMR, GC, and GC-MS analyses indicated the presence of a mixture containing an N-confused dipyrromethane. Characterization, data for Me-1a: mp 90-91° C.; $^1$H NMR (THF-d$_8$) δ 2.22 (s, 6H), 5.32 (s, 1H), 5.55-5.58 (m, 2H), 6.06-6.08 (m, 2H), 7.13-7.26 (m, 5H), 10.14 (br s, 2H); $^{13}$C NMR (THF-d$_8$) δ 21.8, 45.5, 109.4, 115.1, 121.6, 127.2, 128.9, 129.4, 136.8, 143.7; FAB-MS obsd 314.0918, calcd 314.0911 ($C_{17}H_{18}N_2S_2$).

Solventless Synthesis.

A mixture of benzaldehyde (85.2 mg, 0.802 mmol) and Me-4 (182 mg, 1.61 mmol, 2.0 equiv) was treated with TFA (6.2 μL, 80 μmol, 0.1 equiv) at room temperature. After 15 min, the reaction mixture became viscous and the stirring was very slow. Benzaldehyde was completely consumed within 1 h (by TLC). Workup and purification as described above gave Me-1a (0.12 g, 47%) with characterization data consistent with those described above.

Stepwise Synthesis.

A solution of pyrrole Me-8a (30.0 mg, 0.138 mmol) in THF/MeOH (3.0 mL, 10:1) was treated with NaBH$_4$ (15.7 mg, 0.415 mmol) at room temperature for 20 min. The reaction mixture was poured in a mixture of saturated aqueous NH$_4$Cl (10 mL) and CH$_2$Cl$_2$ (10 mL). The organic phase was separated, washed with water, dried (Na$_2$SO$_4$), and concentrated to dryness. A mixture of the resulting residue and pyrrole Me-4 (15.6 mg, 0.138 mmol) was dissolved in toluene (1.3 mL) and treated with InCl$_3$ (30.5 mg, 0.139 mmol) at room temperature. After 30 min, the reaction mixture was washed with 1 M aqueous NaOH. The organic layer was dried (Na$_2$SO$_4$), concentrated, and chromatographed [silica, hexanes/ethyl acetate (8:1)], affording a yellow oil (20 mg, 45%) that solidified after 24 h at −15° C. Characterization data were consistent with those described above.

General Procedure for Dipyrromethane Synthesis Using an n-Decylthio α-Pyrrole Protecting Group, Exemplified for 5-Phenyldipyrromethane (1a).

A mixture of benzaldehyde (0.796 g, 7.50 mmol) and Decyl-4 (3.95 g, 16.5 mmol) in the absence of any solvent was treated with InCl3 (0.332 g, 1.50 mmol) in a loosely closed reaction vessel without deaeration. The heterogeneous mixture was stirred magnetically at room temperature for 16 h. The resulting violet mixture was treated with hexanes (5 mL), affording a brownish mixture. The mixture was filtered through a sintered glass funnel. The filtered material was washed with a small amount of hexanes. The filtrate was concentrated to dryness, affording a brown residue. The flask containing the crude brown residue was placed on a balance.

A solid portion of 30.0 g of wet Raney nickel was removed from a Raney-nickel-THF slurry by a spatula and added directly to the flask containing the brown residue. Reagent grade THF (5.0 mL) was added to wash the inner walls of the flask. The mixture was stirred at room temperature for 1 h. The mixture was filtered through a sintered glass funnel to remove the Raney nickel. The filtered material was washed with THF (~150 mL). The filtrate was concentrated to dryness. The resulting crude residue was dissolved in a small quantity of hexanes/toluene (1:2) and placed on top of a silica pad (3 cm diameter×2 cm in height). The silica pad was eluted with hexanes/toluene [(1:2), ~200 mL]. The first fraction contained 2-benzyl-5-(methylthio)-pyrrole, 2-(methylthio)pyrrole, and unknown pyrrolic byproducts as determined by GC analysis. The second fraction contained predominantly the title compound accompanied by a trace amount of the byproducts. The second fraction was concentrated to dryness. The resulting yellowish solid was treated with hexanes (~20 mL), and the slurry was heated until the solvent refluxed. After a few minutes, the slurry was filtered. The filtrate, which contained less polar byproducts and only a small quantity of product, was discarded. The filtered material (white) was washed with a small amount of hexanes and then collected, affording a white solid (1.10 g, 66%): mp 98-99° C.; $^1$H NMR δ 5.49 (s, $^1$H), 5.92-5.98 (m, 2H), 6.15-6.22 (m, 2H), 6.65-6.75 (m, 2H), 7.22-7.36 (m, 5H), 7.94 (br s, 2H); $^{13}$C NMR δ 43.9, 107.2, 108.4, 117.2, 127.0, 128.4, 128.6, 132.5, 142.0. Anal. Calcd for $C_{15}H_{14}N_2$: C, 81.05; H, 6.35; N, 12.60. Found: C, 81.05; H, 6.44; N, 12.33.

1,9-Bis(methylthio)-5-phenyldipyrrin (Me-6a)

Following a standard procedure, a solution of Me-1a (20.0 mg, 63.6 µmol) in THF (0.64 mL) was treated with DDQ (17.3 mg, 73.2 µmol) at room temperature for 24 h. The mixture was concentrated and chromatographed (hexanes/ethyl acetate (5:1) containing 1% TEA), affording a yellow viscous solid (12 mg, 60%): NMR (THF-$d_8$) δ 2.64 (s, 6H), 6.32 (d, J=4.4 Hz, 2H), 6.45 (d, J) 4.4 Hz, 2H), 7.43 (s, 5H); $^{13}$C NMR (THF-$d_8$) δ 16.0, 30.7, 119.0, 128.6, 128.9, 129.4, 131.7, 134.2, 138.0, 142.2, 151.8; FAB-MS obsd 313.0836, calcd 313.0833 [(M+H)$^+$, M=$C_{17}H_{16}N_2S_2$]; $\lambda_{abs}$ 336, 474 nm.

Dibutyl[5,10-dihydro-1,9-bis(methylsulfonyl)-5-phenyldipyrrinato]tin(IV) (Me-7a)

Following the solventless synthesis of Me-1a described above, a mixture of benzaldehyde (85.2 mg, 0.802 mmol) and Me-4 (182 mg, 1.61 mmol) was treated with $InCl_3$ (17.8 mg, 80.0 µmol) at room temperature. After 1 h, TLC showed the reaction to be complete. The reaction mixture was diluted with ethyl acetate and washed with 0.1 M aqueous NaOH. The organic phase was separated, washed with water, dried ($Na_2SO_4$), and concentrated to dryness. The residue was dissolved in $CH_2Cl_2$ (15 mL) and cooled to 0° C. in an ice bath. The solution was treated with m-CPBA (428 mg, 77% purity from commercial supplier, 1.91 mmol), and the mixture was stirred at 0° C. for 4 h. After warming to room temperature, the reaction mixture was washed with saturated aqueous $NaHCO_3$. The organic phase was separated, washed with water, dried ($Na_2SO_4$), and concentrated. Following a standard method (Tamaru, S.-I. et al., *J. Org. Chem.* 2004, 69, 765-777), the crude mixture was redissolved in $CH_2Cl_2$ (3 mL). TEA (0.265 mL, 1.91 mmol) was added. The reaction mixture was treated with $Bu_2SnCl_2$ (193 mg, 0.635 mmol) for 30 min and then filtered through a silica pad ($CH_2Cl_2$), affording a pale yellow viscous oil (25 mg, 5%): $^1$H NMR (THF-$d_8$) δ 0.70-0.77 (m, 6H), 0.86-1.21 (m, 4H), 1.28-1.42 (m, 4H), 1.58-1.67 (m, 4H), 3.14 (s, 6H), 5.54 (s, 1H), 6.22 (d, J=3.2 Hz, 2H), 6.89 (d, J=3.2 Hz, 2H), 6.98-7.01 (m, 2H), 7.09-7.20 (m, 3H); $^{13}$C NMR (THF-$d_8$) δ 13.84, 13.94, 26.6, 27.11, 27.14, 27.4, 28.0, 29.4, 45.9, 114.1, 116.4, 127.1, 128.6, 129.0, 132.6, 144.8, 145.9; FAB-MS obsd 611.1087, calcd 611.1060 [(M+H)$^+$, M=$C_{25}H_{34}N_2O_4S_2Sn$].

The foregoing is illustrative of the present invention, and is not to be construed as limiting thereof. The invention is defined by the following claims, with equivalents of the claims to be included therein.

That which is claimed is:

1. A method for the synthesis of a porphyrin rod, comprising the steps of:
   (a) providing a compound of the formula A'-L-B, wherein A is a 1,9-bis(thio)dipyrromethane, L is a linker group or covalent bond, and B is a dipyrromethane-1,9-dicarbinol;
   (b) providing a compound of the formula C-L-D; wherein C is a dipyrromethane, L is a linker group or covalent bond, and D is a 1,9-diacyldipyrromethane or surface attachment group;
   (c) condensing said compound of formula A'-L-B with said compound of formula C-L-D to produce an elongated compound of formula A-L-D, wherein A is a 1,9-bis(thio)dipyrrin, L is a linker group, and D said a 1,9-diacyldipyrromethane or surface attachment group, with said linker group comprising at least one porphyrinic macrocycle.

2. The method of claim 1, further comprising the steps of:
   (d) reducing said elongated compound of formula A-L-D to produce an elongated compound of the formula A'-L-B, wherein A is a 1,9-bis(thio)dipyrromethane, L is said linker group or covalent bond, and B is a dipyrromethane-1,9-dicarbinol;
   (e) reacting said elongated compound of formula A'-L-B with a dipyrromethane to produce a compound of the formula A-L-E, wherein E is a porphyrinic macrocycle;
   (f) desulfurizing and reducing said compound of formula A-L-E to produce a compound of formula C-L-E, wherein C is a dipyrromethane; and then
   (g) reacting said compound of formula C-L-E with a dipyrromethane-1,9-dicarbinol to produce a compound of the formula F-L-E, wherein F is a porphyrinic macrocycle.

3. The method of claim 2, wherein said compound of formula F-L-E contains at least one surface attachment group, said method further comprising the step of:
   (h) coupling said compound of formula F-L-E to a substrate to produce a molecular memory device.

4. The method of claim 1, further comprising the steps of:
   (d) desulfurizing and reducing said elongated compound of formula A-L-D to produce an elongated compound of the formula C-L-D; wherein C is a dipyrromethane, L is said linker group or covalent bond, and D is a 1,9-diacyldipyrromethane;
   (e) reacting said compound of formula C-L-D with a dipyrromethane-1,9-dicarbinol to produce a compound of the formula F-L-D, wherein F is a porphyrinic macrocycle; and then
   (f) reducing said compound of formula F-L-D to produce a compound of formula F-L-B, wherein B is a dipyrromethane-1,9-dicarbinol; and then
   (g) reacting said compound of formula F-L-B with a dipyrromethane to produce a compound of the formula F-L-E, wherein E is a porphyrinic macrocycle.

5. The method of claim 4, wherein said compound of formula F-L-E contains at least one surface attachment group, said method further comprising the step of:

(h) coupling said compound of formula F-L-E to a substrate to produce a molecular memory device.

6. The method of claim 1, wherein, for said compound of the formula A'-L-B:

A' is a group of the formula:

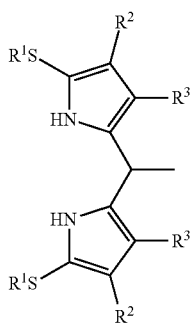

(A')

wherein $R^1$, $R^2$, and $R^3$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups; and B is a group of the formula:

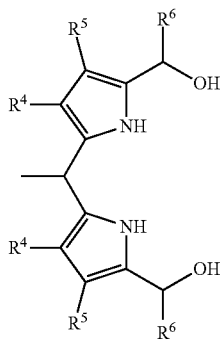

(B)

wherein $R^4$, $R^5$, and $R^6$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups.

7. The method of claim 1, wherein, for said compound of the formula C-L-D:

C is a group of the formula:

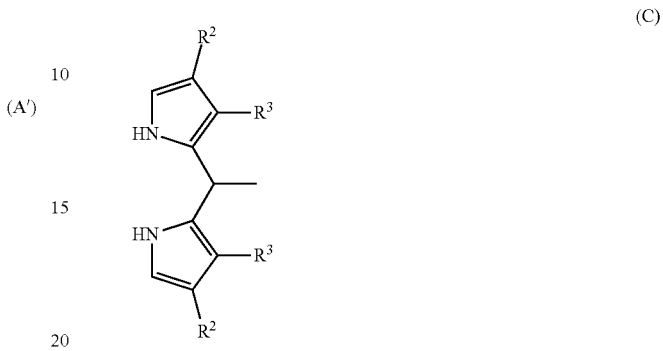

(C)

wherein $R^2$ and $R^3$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups; and D is a group of the formula:

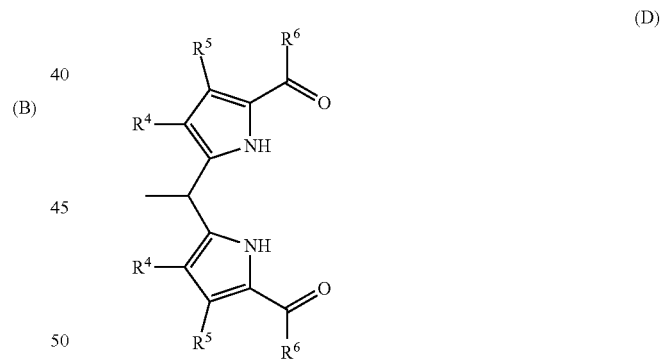

(D)

wherein $R^4$, $R^5$, and $R^6$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups.

* * * * *

UNITED STATES PATENT AND TRADEMARK OFFICE
CERTIFICATE OF CORRECTION

PATENT NO. : 8,618,281 B2  
APPLICATION NO. : 13/600808  
DATED : December 31, 2013  
INVENTOR(S) : Lindsey et al.

Page 1 of 1

It is certified that error appears in the above-identified patent and that said Letters Patent is hereby corrected as shown below:

In the Specification

Column 1, Lines 18-21: Please correct the Government Funding Clause in its entirety to read as follows:

-- This invention was made with government support under grant number GM-036238 awarded by the National Institutes of Health. The government has certain rights to this invention. --

Signed and Sealed this  
Twenty-fourth Day of June, 2014

Michelle K. Lee  
*Deputy Director of the United States Patent and Trademark Office*